(12) United States Patent
Hariyama et al.

(10) Patent No.: US 8,253,935 B2
(45) Date of Patent: Aug. 28, 2012

(54) DISK SURFACE INSPECTION APPARATUS, INSPECTION SYSTEM THEREOF, AND INSPECTION METHOD THEREOF

(75) Inventors: Tatsuo Hariyama, Fujisawa (JP);
Hideaki Sasazawa, Yokohama (JP);
Minoru Yoshida, Yokohama (JP);
Shigeru Serikawa, Chigasaki (JP)

(73) Assignee: Hitachi High-Technologies Corporation, Tokyo (JP)

( * ) Notice: Subject to any disclaimer, the term of this patent is extended or adjusted under 35 U.S.C. 154(b) by 248 days.

(21) Appl. No.: 12/694,297

(22) Filed: Jan. 27, 2010

(65) Prior Publication Data
US 2010/0201975 A1    Aug. 12, 2010

(30) Foreign Application Priority Data
Feb. 10, 2009  (JP) .................................. 2009-028453

(51) Int. Cl.
*G01N 21/00*   (2006.01)
(52) U.S. Cl. .................................................. 356/237.2
(58) Field of Classification Search .................. None
See application file for complete search history.

(56) References Cited

U.S. PATENT DOCUMENTS

| 4,589,773 A * | 5/1986 | Ido et al. ....................... 356/623 |
| 2007/0057184 A1 * | 3/2007 | Uto et al. ........................ 250/310 |
| 2009/0184234 A1 * | 7/2009 | Shindo et al. ................. 250/206 |

FOREIGN PATENT DOCUMENTS

JP    2001-066263    3/2001

* cited by examiner

*Primary Examiner* — Tu Nguyen
(74) *Attorney, Agent, or Firm* — Antonelli, Terry, Stout & Kraus, LLP.

(57) ABSTRACT

The invention has a function of preparing a data base for a relation between a defect shape and an arrangement for the optical system capable of detecting the shape at high sensitivity and automatically adjusting the arrangement for the optical system. As the method of preparing the data base, a method of using optical simulation or an experimental method of using a sample having an optical shape is applied. A pinhole position and a beam size are adjusted automatically so as to attain the optimal arrangement for the optical system to an inputted defect shape based on the data base.

15 Claims, 31 Drawing Sheets

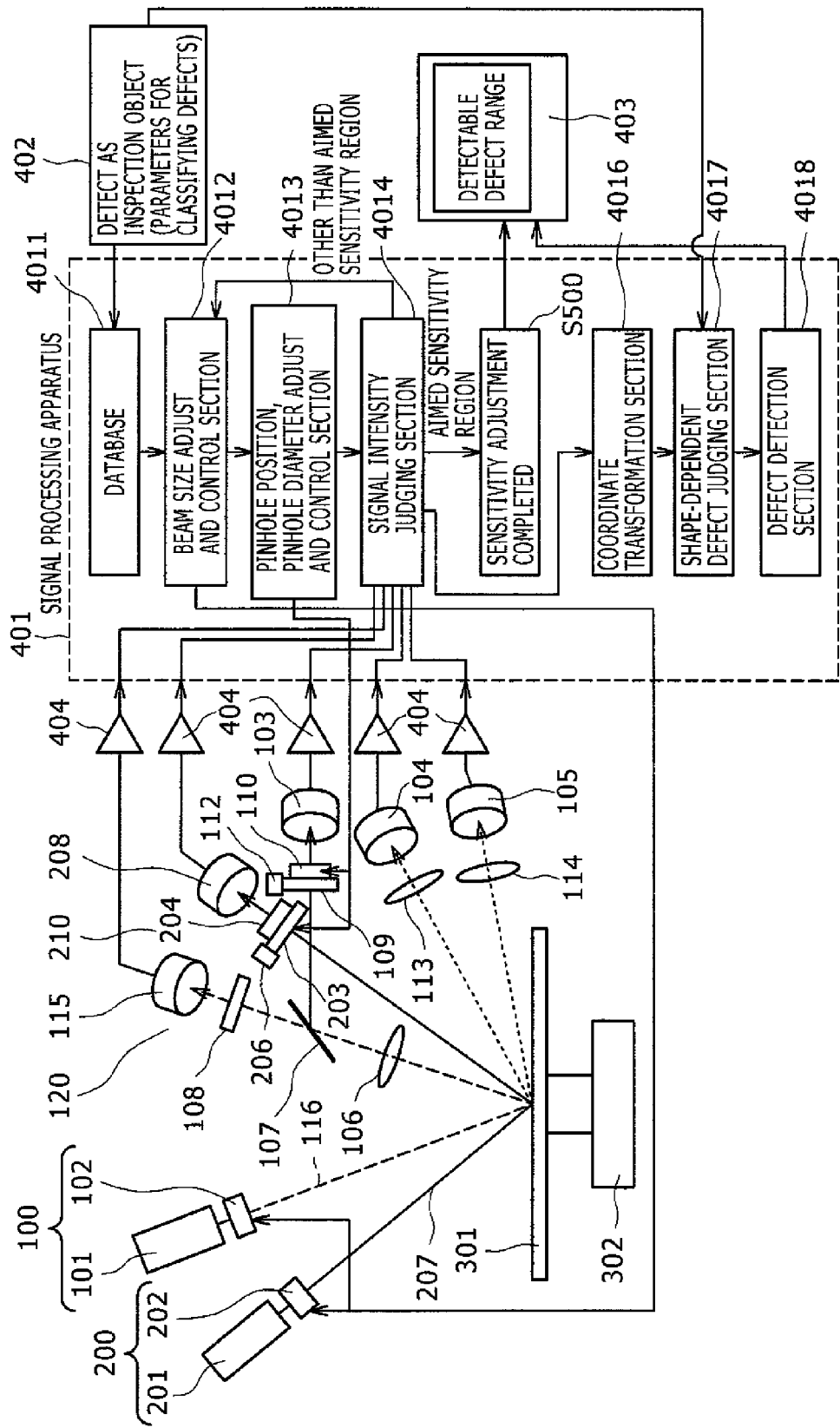

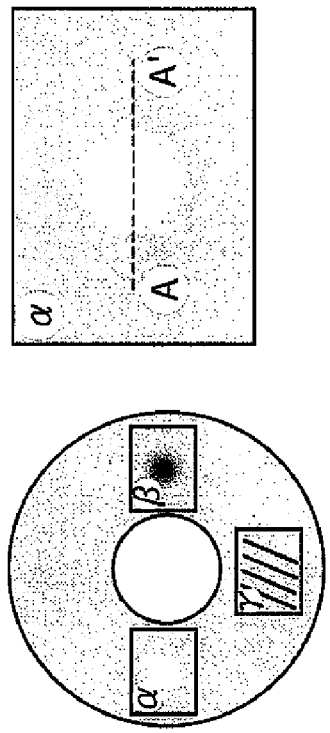
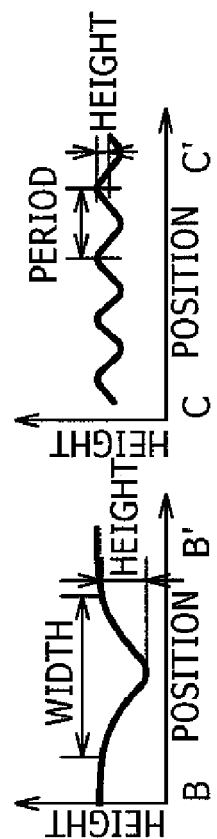

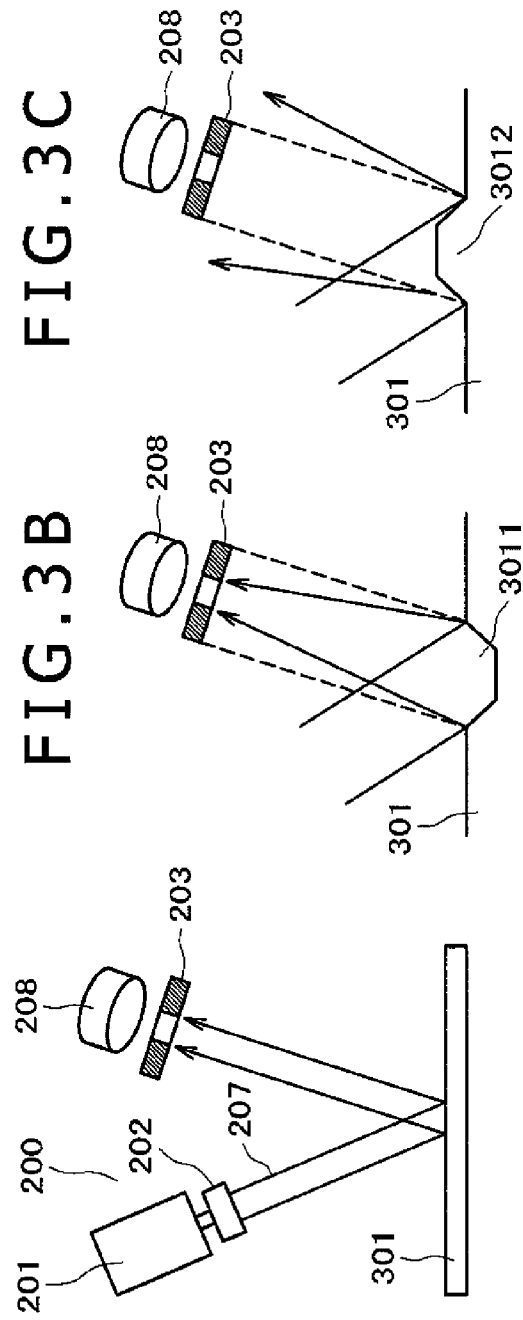
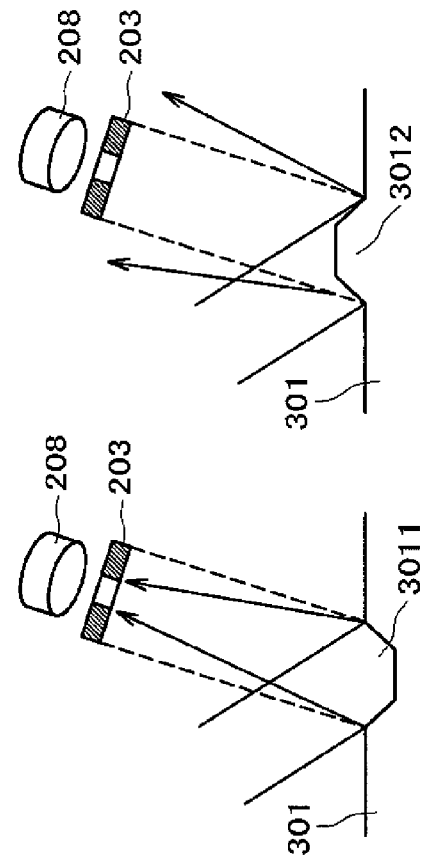
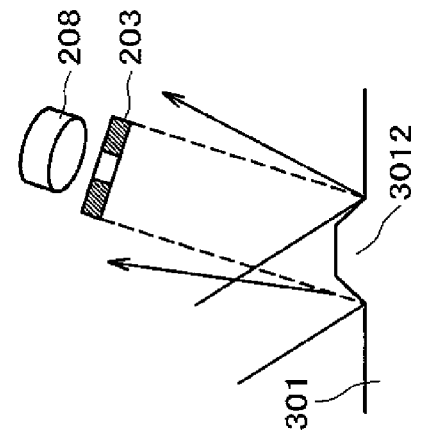
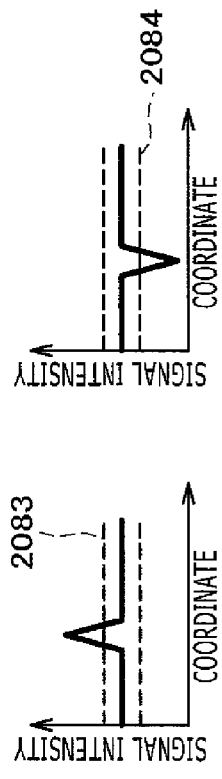
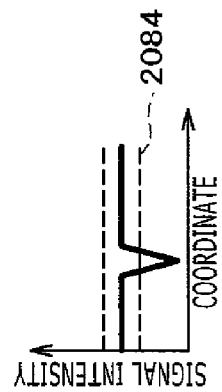

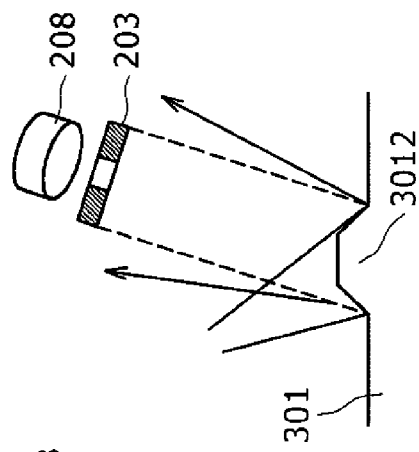
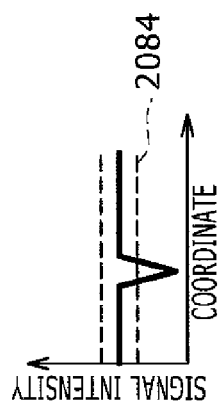
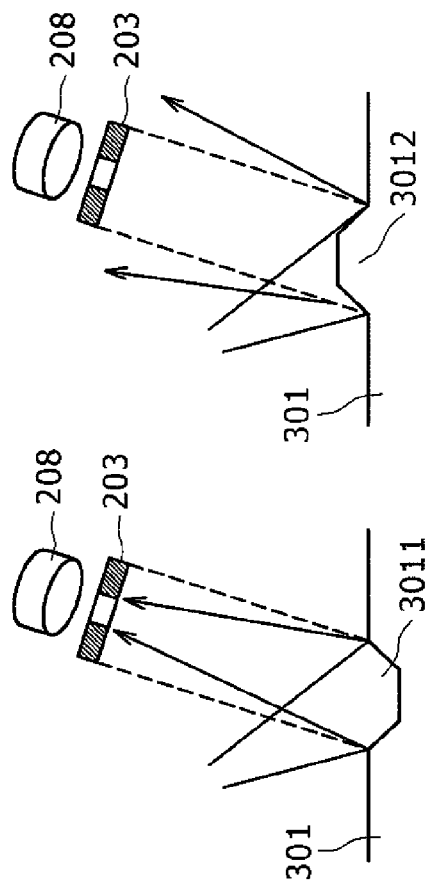
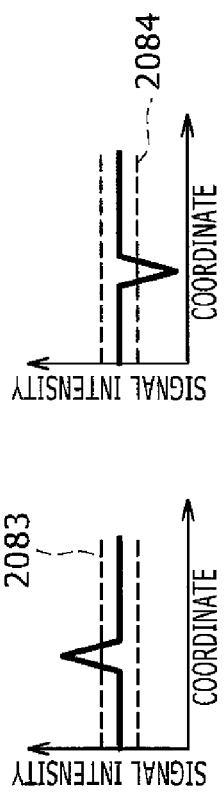
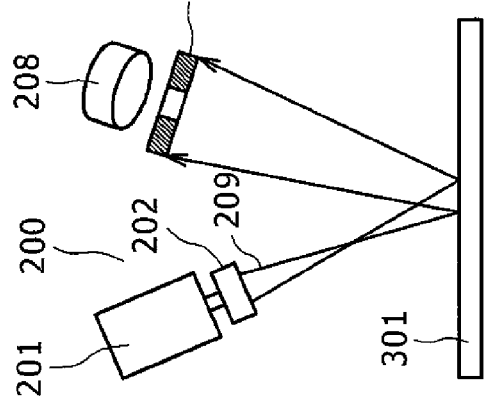

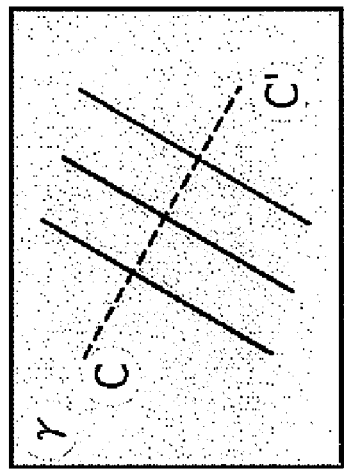
FIG.5A
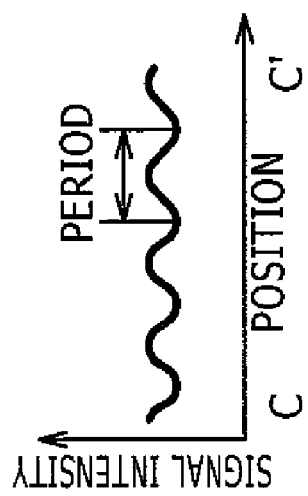
FIG.5B
FIG.5C
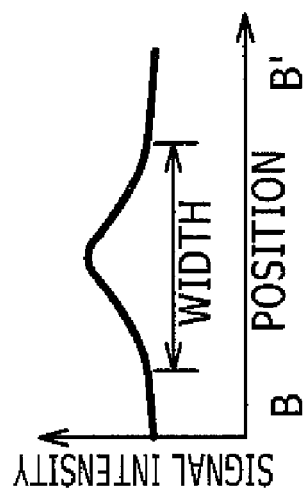
FIG.5D
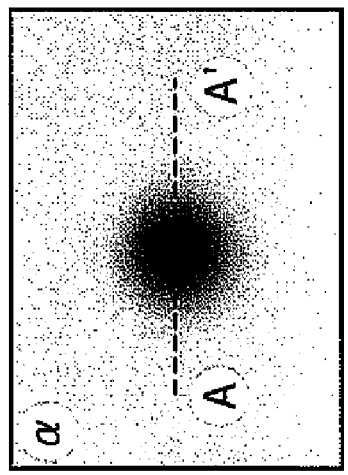
FIG.5E
FIG.5F
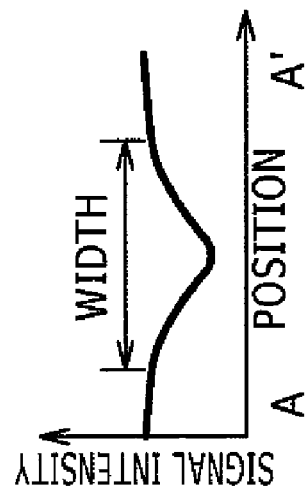

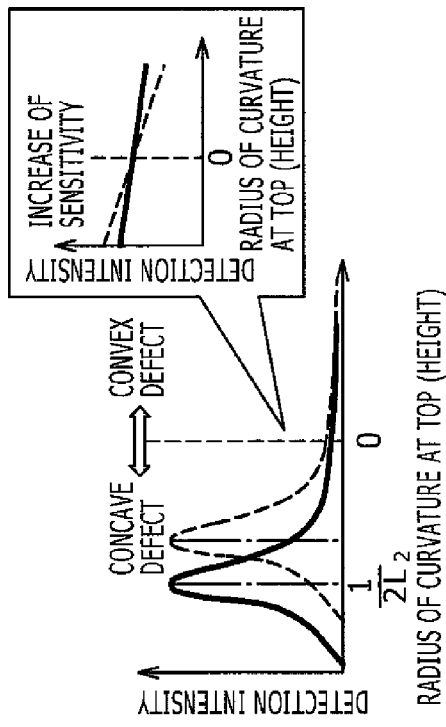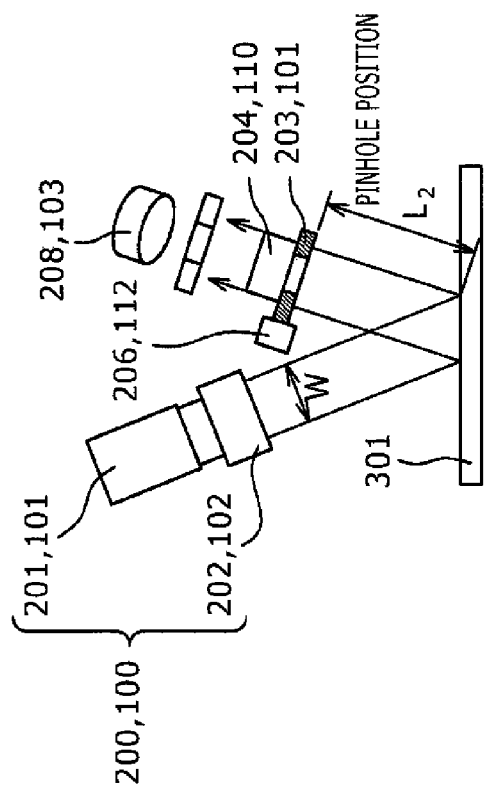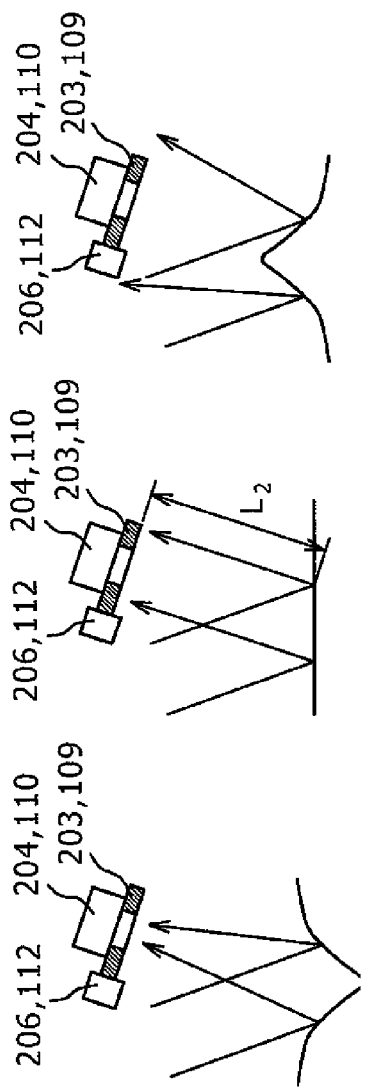

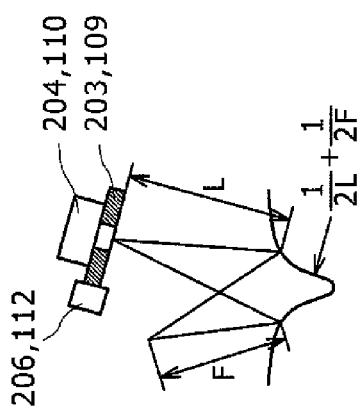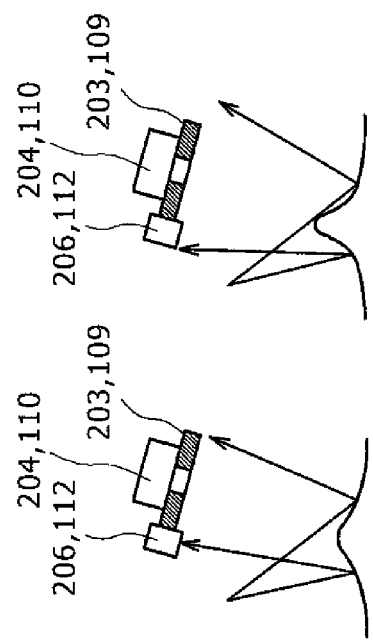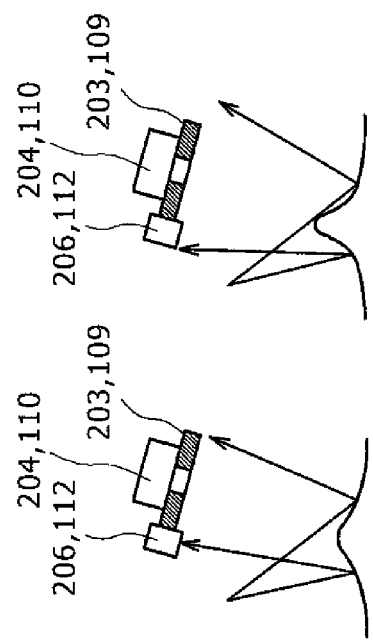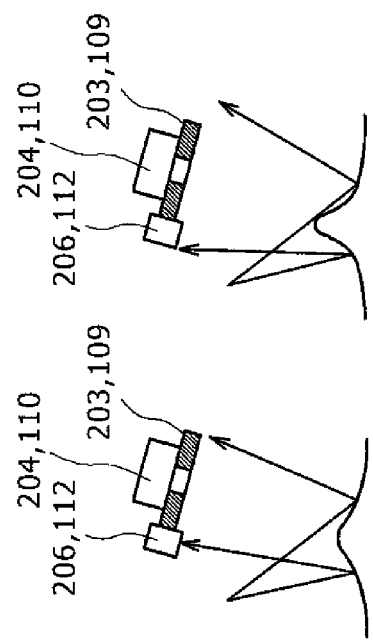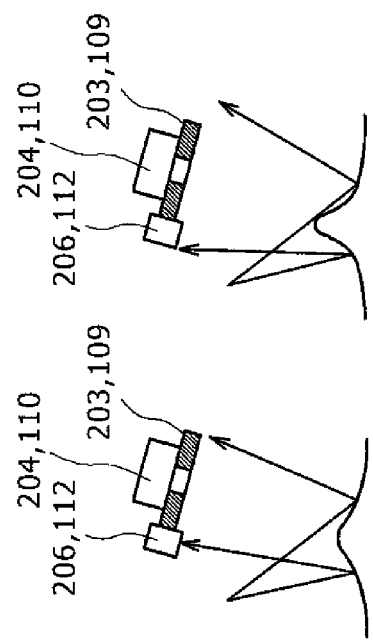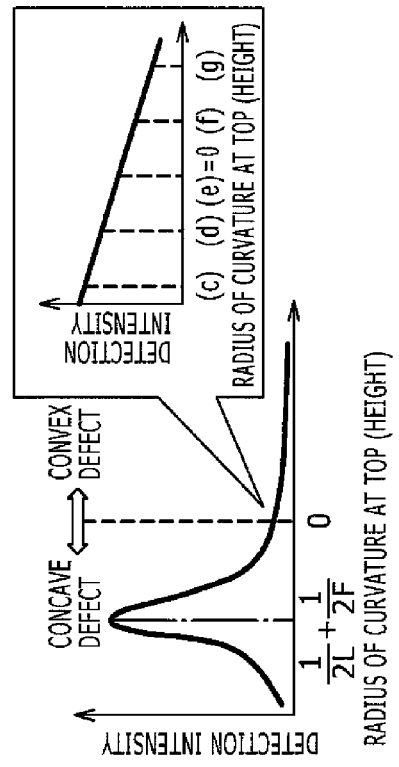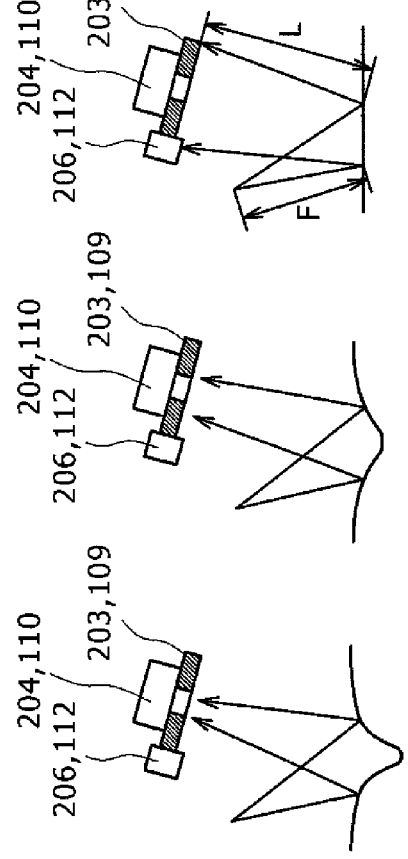
FIG.14A   FIG.14B
FIG.14C   FIG.14D   FIG.14E   FIG.14F   FIG.14G

FIG.16A
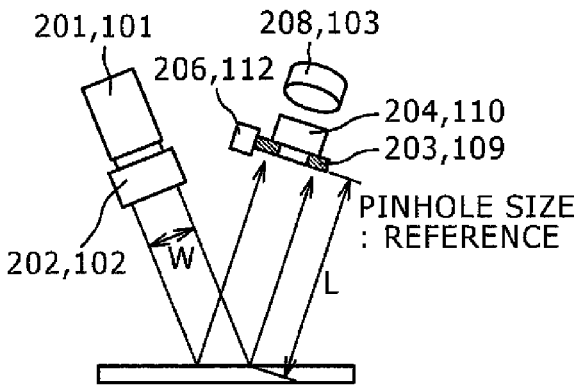
FIG.16B
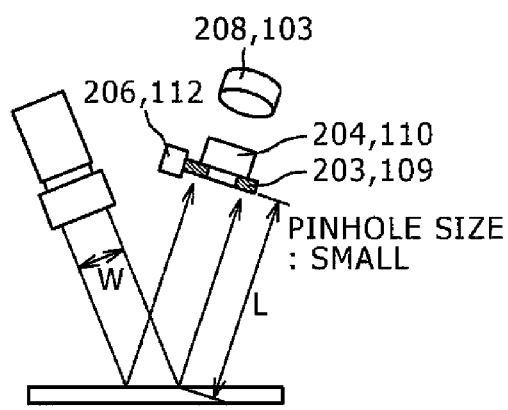
FIG.16C
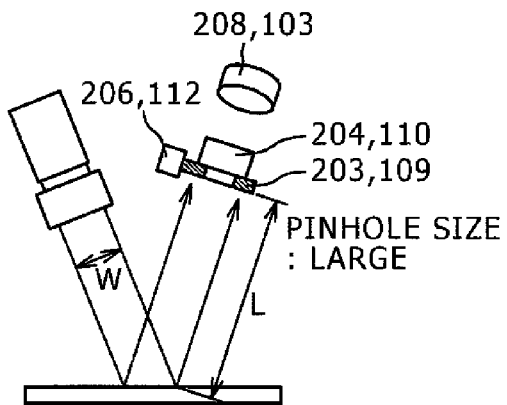
FIG.16D
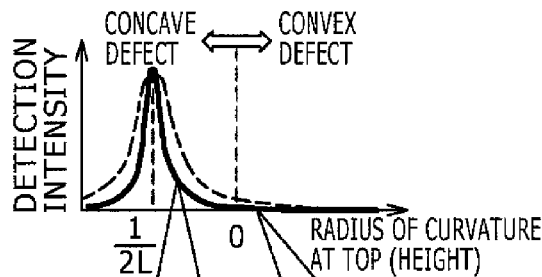
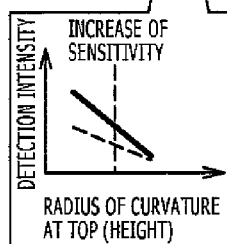
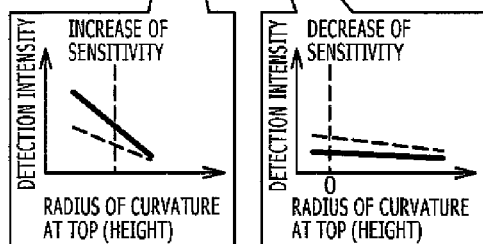
FIG.16E
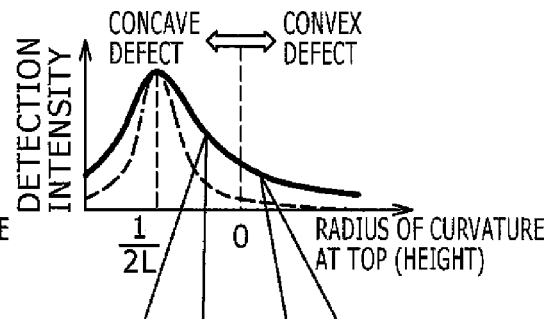
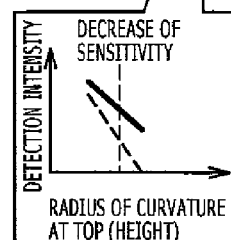
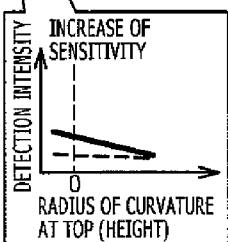

ROUGHNESS SAMPLE A

ROUGHNESS SAMPLE B

ROUGHNESS SAMPLE C

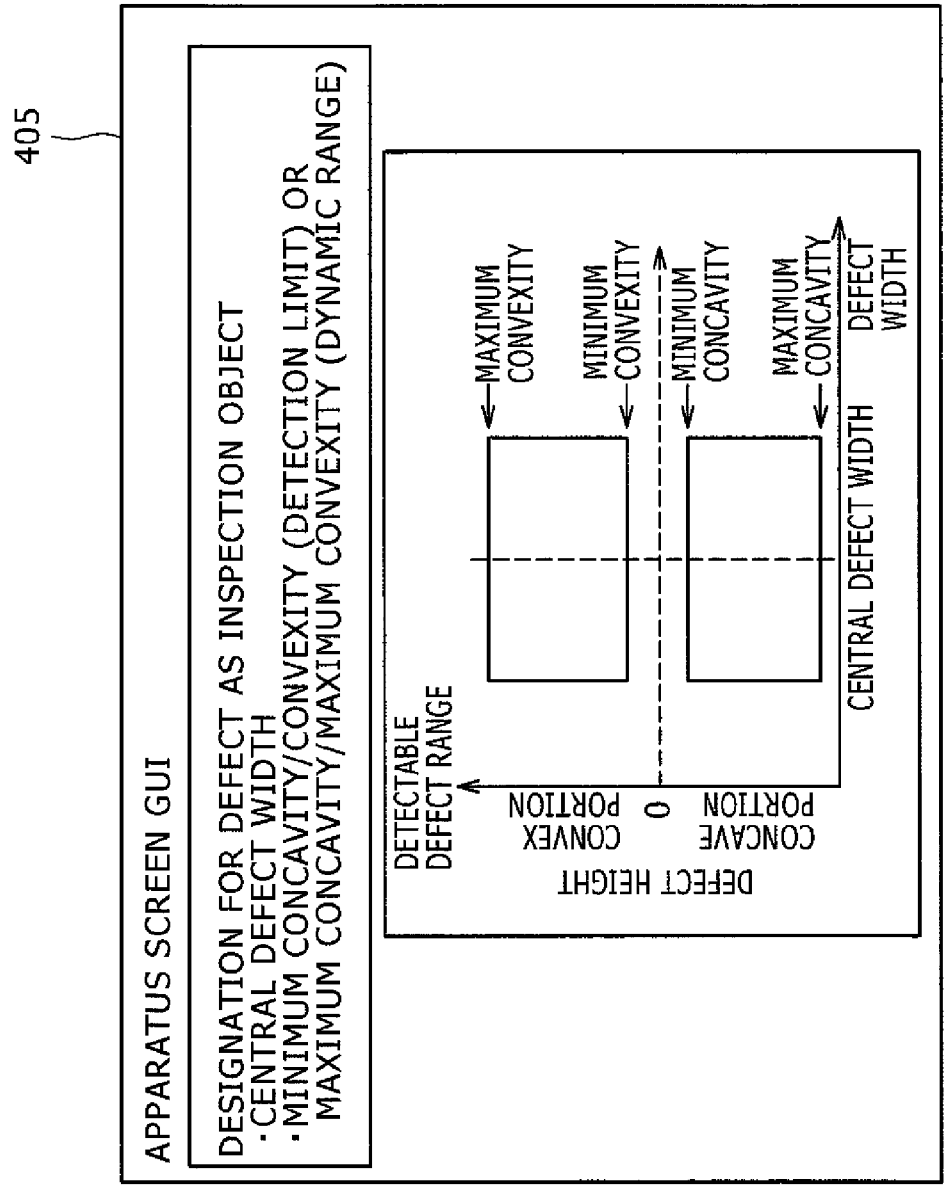

DISK SURFACE INSPECTION APPARATUS, INSPECTION SYSTEM THEREOF, AND INSPECTION METHOD THEREOF

BACKGROUND

The invention relates to a disk surface inspection apparatus capable of adjusting the sensitivity of an inspection optical system to a defect as a target of inspection and reducing the instrumental error between apparatuses of the optical system, an inspection system thereof, and an inspection method thereof.

Disks formed of glass, silicon wafer, etc. are used as materials for information recording media or semiconductors. Since the properties of products are deteriorated, when defects are present on the surface of the materials, inspection is conducted by a disk surface inspection apparatus. The disk surface inspection apparatus detects defects present on the disk surface. The defects include various kinds of defects, for example, dusts (particles) attached to the surface, stains, scratches caused by obstacles, fine concave portions (pits) and convex portions (bumps) or moderately inclined convex portions (bumps) or concave portions (dimples), deformation at disk ends formed by collision upon handling of disks (handling damages), and polishing traces on the disk surface (glides). As an effective detection method for such various types of defects, it has been used a method of detecting defects by irradiating a laser beam to a disk surface, and receiving optical feature, that is, reflection light or scattered light of the laser beam detected differently depending on the shape and the size of each of the defects respectively by a disk surface detection apparatus as described in JP-A No. 2001-66263.

SUMMARY

One of the problems of the conventional type disk surface inspection apparatus in adjusting an optical system before inspection by using a defect sample as an inspection target is manually adjusting a beam spot diameter and a pinhole position so as to obtain sufficient sensitivity for detection of the sample. Accordingly, if a new kind of defect occurs, it is necessary to manually adjust the arrangement for the optical system again.

Further, it is necessary to adjust the arrangement experimentally by using a defect sample. But sometimes it takes a long time for the adjustment. Further, since the detection sensitivities of the inspection apparatuses have been individually adjusted by manual by using a defect sample, it has a potential to causes an instrumental error.

In view of the foregoing problem of the conventional type disk surface inspection apparatus, this invention provides a disk surface inspection apparatus capable of automatically adjusting an optical system so as to maintain a sufficient sensitivity in the detection of defects (particularly, low aspect defects). This invention also provides an inspection system thereof, and an inspection method thereof.

The invention provides a disk surface inspection apparatus including a projection optical system for irradiating a laser beam to a disk surface, a receiving optical system for receiving a normal reflection light of the laser beam obtained from the disk surface irradiated by the projection optical system through a photoreceiving surface, and a signal processing section for inspecting the state of the disk surface based on signals obtained from the receiving optical system, the apparatus including:

a first adjusting means for adjusting a beam spot diameter on the disk surface of the laser beam irradiated by the projection optical system, and second adjusting means for moving and adjusting a position of the photoreceiving surface for receiving a normal reflection light by the receiving optical system in a direction of an optical axis, thereby adjusting a photoreception amount to the photoreceiving surface.

The apparatus of the invention further has a data base that determines and stores a beam spot diameter adjusting amount, and a moving and adjusting amount of the photoreceiving surface and a photoreception adjusting amount to the photoreceiving surface capable of obtaining sufficient sensitivity for detection of a defect of an optional shape by previous simulation or experiment, wherein the apparatus obtains the beam spot diameter adjusting amount, and the moving and adjusting amount of the photoreceiving surface and the photoreception adjusting amount to the photoreceiving surface capable of obtaining sufficient sensitivity in accordance with a defect shape as an inspection target inputted from the data base, and the first adjusting means conducts adjustment based on the obtained beam spot diameter adjusting amount, and the second adjust means conducts adjustment based on the obtained moving and adjusting amount of the photoreceiving surface and the photoreception adjusting amount to the photoreceiving surface.

Further, according to the invention, the data base stores known relevant data for a detection intensity detected by the receiving optical system to the defect of an optional shape in a relation between the beam spot diameter adjusting amount, and the moving and adjusting amount of the photoreceiving surface and the photoreception adjusting amount to the photoreceiving surface, and the signal processing section estimates the defect shape based on the known relevant data stored in the data base in view of the detection intensity based on signals obtained from the receiving optical system.

Further, the apparatus of the invention includes first and second projection optical systems for irradiating each of first and second laser beams to a disk surface, first and second receiving optical systems for receiving each of first and second normal reflection lights of the first and the second laser beams obtained from the disk surface irradiated by each of the first and the second projection optical systems, and a signal processing section that inspects the state of the disk surface based on signals obtained from each of the first and the second receiving optical systems, the apparatus further including:

first adjusting means for adjusting each of the beam spot diameters at the disk surface of the irradiated laser beam by each of the first and the second projection optical systems, and second adjusting means for moving and adjusting a position for each of the photoreceiving surfaces that receives each of the first and the second normal reflection lights by each of the first and the second receiving optical systems in a direction of an optical axis thereby adjusting a photoreceiving amount to each of the photoreceiving surfaces.

Further, the apparatus according to the invention includes a data base that determines and stores a beam spot diameter adjusting amount by each of the first and the second projection optical systems, and a moving and adjusting amount of the photoreceiving surface and a photoreception adjusting amount to the photoreceiving surface by each of the first and the second receiving optical systems capable of obtaining sufficient sensitivity for detection of a defect of an optional shape by previous simulation or experiment, wherein the apparatus obtains the beam spot diameter adjusting amount by each of the first and the second projection optical systems, and the moving and adjusting amount of the photoreceiving surface and the photoreception adjusting amount to the photoreceiving surface by each of the first and the second receiving optical systems capable of obtaining the sufficient sensitivity in accordance with a defect shape as an inspection target inputted from the data base, and the first adjusting means conducts adjustment based on the obtained beam spot diameter adjusting amount by each of the first and the second projection optical systems, and the second adjusting means conducts adjustment based on the obtained moving and adjusting amount of the photoreceiving surface and the photoreception adjusting amount to the photoreceiving surface by each of the first and the second receiving optical system.

Further, according to the invention, the first laser beam is irradiated to the disk surface while restricted more finely than the second laser beam. Further, according to the invention, the first receiving optical surface has a branching optical system for branching the reflection light of the first laser beam obtained from the disk surface into first and second optical paths, a first photoreceiving device for receiving a scattered light while cutting off the normal reflection light in the first optical path branched at the branching optical system, and a second photoreceiving device for receiving the normal reflection light through the photoreceiving surface in the second optical path branched at the branching optical system.

Further, according to the invention, the data base stores known relevant data of a detection intensity detected by each of the first and the second receiving optical systems to a defect of an optional shape in a relation between the beam spot diameter adjusting amount by each of the first and the second projection optical systems and the moving and adjusting amount of the photoreceiving surface and the photoreception adjusting amount to the photoreceiving surface by each of the first and the second receiving optical systems, and the signal processing section estimates the defect shape based on the known relevant data stored in the data base in view of the detection intensity (detection signal waveform) based on the signals obtained from each of the first and the second receiving optical systems.

Further, the invention provides a disk surface inspection system including plural disk surface inspection apparatuses each including a projection optical system for irradiating a laser beam to a disk surface, a receiving optical system for receiving a normal reflection light of the laser beam obtained from the disk surface irradiated by the projection optical system through a photoreceiving surface, and a signal processing section that inspects the state of the disk surface based on signals obtained from the receiving optical system, the apparatuses further including:

first adjusting means for adjusting the beam spot diameter on the disk surface of the laser beam irradiated by the projection optical system, and second adjusting means for moving and adjusting a position of the photoreceiving surface for receiving the normal reflection light by the receiving optical system in a direction of an optical axis, thereby adjusting a photoreception amount to the photoreceiving surface, wherein a data base that determines and stores a beam spot diameter adjusting amount and a moving and adjusting amount of the photoreceiving surface and a photoreception adjusting amount to the photoreceiving surface capable of obtaining sufficient sensitivity for detection to a defect of an optional shape by previous simulation or experiment is used in common among the plural disk surface inspection apparatuses.

Further, the invention provides a disk surface inspection method including a first step of inputting the shape information of a defect as an inspection target, a second step of automatically selecting, from a data base, a beam spot diameter, a pinhole position, and a pinhole diameter capable of obtaining sufficient sensitivity for detection by the inputted defect shape information, a third step of automatically adjusting the beam spot diameter, and a fourth step of automatically adjusting the pinhole position and the pinhole diameter. After the fourth step, an actual defect sample of a known shape is measured optionally. For the sample, a signal intensity to be obtained as an aimed value is previously known by the data base. The result of measurement and the aimed value are compared and, when the measured value is in a region near the aimed sensitivity, it is judged that the adjustment has been completed and when it is not in the region near the aimed sensitivity, the beam spot diameter, the pinhole position, and the pinhole diameter are again adjusted finely and adjustment is continued until the measured value enters the aimed sensitivity region. According to this method, the sensitivity can be adjusted finely to an optional defect shape. As the fifth step, a detectable defect range can be displayed on an output screen by the adjusted optical system.

Further, the data base is used in common among plural apparatus, an optical system is adjusted in a reference apparatus so as to obtain sensitivity to a defect as an inspection target, and adjustment is conducted in the same manner as for other apparatuses thereby reducing an instrumental error.

Further, the defect shape can be estimated from the detection signal waveform conversely based on the data base.

These features and advantages of the invention will be apparent from the following more particular description of preferred embodiments of the invention, as illustrated in the accompanying drawings.

BRIEF DESCRIPTION OF THE DRAWINGS

FIG. 1 is a configurational view showing an embodiment of a disk surface inspection apparatus according to the invention;

FIG. 2A is a plan view for an entire disk;

FIG. 2B is an enlarged view for a portion α where a bump defect occurs;

FIG. 2C is an enlarged view for a portion β where a dimple defect occurs;

FIG. 2D is an enlarged view for a portion γ where a wrinkle defect occurs;

FIG. 2E is a view showing a cross sectional profile in FIG. 2B;

FIG. 2F is a view showing a cross sectional profile in FIG. 2C;

FIG. 2G is a view showing a cross sectional profile in FIG. 2D;

FIG. 3A is a view showing the outline of an optical system for irradiating and detecting a concave/convex defect of a low aspect ratio at a disk surface by a parallel light;

FIG. 3B is a view showing the outline of an optical system for detecting a reflection light from a concave defect of a low aspect ratio at the disk surface irradiated by the parallel light;

FIG. 3C is a view showing the outline of an optical system for detecting a reflection light from a convex defect of a low aspect ratio at the disk surface irradiated by the parallel light;

FIG. 3D is a view showing the intensity distribution of an output signal of the optical system that detects the concave defect of the low aspect ratio irradiated by the parallel light in FIG. 3B;

FIG. 3E is a view showing the intensity distribution of an output signal of the optical system that detects the convex defect of a low aspect ratio irradiated by the parallel light in FIG. 3C;

FIG. 4A is a view showing the outline of an optical system for irradiating and detecting a concave/convex defect of a low aspect ratio at the disk surface by a converging light;

FIG. 4B is a view showing the outline of an optical system for detecting a reflection light from a concave defect of a low aspect ratio at the disk surface irradiated by the converging light;

FIG. 4C is a view showing the outline of an optical system for detecting a reflection light from a convex defect of a low aspect ratio at the disk surface irradiated by the converging light;

FIG. 4D is a view showing the intensity distribution of an output signal of the optical system that detects the concave defect of a low aspect ratio irradiated by the converging light in FIG. 4B;

FIG. 4E is a view showing the intensity distribution of an output signal of the optical system that detects the convex defect of a low aspect ratio irradiated by the converging light in FIG. 4C;

FIG. 5A is an enlarged view for a portion α where a bump defect occurs;

FIG. 5B is an enlarged view for a portion β where a dimple defect occurs;

FIG. 5C is an enlarged view for a portion γ where a wrinkle defect occurs;

FIG. 5D is a view showing the intensity distribution of an output signal of the optical system that inspects the defect in FIG. 5A;

FIG. 5E is a view showing the intensity distribution of an output signal of the optical system that inspects the defect in FIG. 5B;

FIG. 5F is a view showing the intensity distribution of an output signal of the optical system that inspects the defect in FIG. 5C;

FIG. 11A is a view showing a positional relation between an irradiation optical system, and a pinhole and a detector in a state of approaching the position of the pinhole to the disk surface further relative to the reference distance L in FIG. 7 in the direction of the optical axis;

FIG. 11B is a graph showing a relation between the radius of curvature at a defect top and a detection intensity detected by the detector in a case of using the optical system having the configuration shown in FIG. 11A;

FIG. 11C is a view showing a positional relation between the incident light/reflection light to a concave defect and the pinhole of the optical system having the configuration shown in FIG. 11A;

FIG. 11D is a view showing a positional relation between the incident light/reflection light to a defect free region and the pinhole of the optical system having the configuration shown in FIG. 11A;

FIG. 11E is a view showing a positional relation between the incident light/reflection light to a convex defect and the pinhole of the optical system having the configuration shown in FIG. 11A;

FIG. 14A is a graph showing a relation between the radius of curvature at a defect top (=height) and a detection intensity in the optical system shown in FIG. 12;

FIG. 14B is a view showing a positional relation between the incident light/reflection light to a concave defect of a large negative radius of curvature and a pinhole of the optical system having the configuration shown in FIG. 12;

FIG. 14C is a view showing a positional relation between the incident light/reflection light to a concave defect of a medium negative radius of curvature and a pinhole of an optical system of the configuration shown in FIG. 12. This is a view showing a relation between the pinhole position and the detection intensity in the optical system shown in FIG. 12;

FIG. 14D is a view showing a positional relation between the incident light/reflection light to a concave defect of a small negative radius of curvature and a pinhole for the optical system having the configuration shown in FIG. 12;

FIG. 14E is a view showing a positional relation between the incident light/reflection light to a defect free region of radius of curvature of 0 and a pinhole for the optical system having the configuration shown in FIG. 12;

FIG. 14F is a view showing a positional relation between the incident light/reflection light to a convex defect of a small positive radius of curvature and a pinhole of the optical system having the configuration shown in FIG. 12;

FIG. 14G is a view showing a positional relation between the incident light/reflection light to a convex defect of a large positive radius of curvature and a pinhole of the optical system having the configuration shown in FIG. 12;

FIG. 16A shows a case where a pinhole has a reference size in the optical system having the configuration shown in FIG. 7;

FIG. 16B shows a case where the size of the pinhole is smaller than the reference size in the optical system of the configuration shown in FIG. 7;

FIG. 16C shows a case where the size of the pinhole is larger than the reference size in the optical system of the configuration shown in FIG. 7;

FIG. 16D is a graph showing a relation between the radius of curvature at the defect top and a detection intensity detected by the detector in a case of using the optical system having the configuration shown in FIG. 16B;

FIG. 16E is a graph showing a relation between the radius of curvature at the defect top and a detection intensity detected by the detector in a case of using the optical system having the configuration shown in FIG. 16C;

FIG. 25 shows a GUI screen of an apparatus for conducting optical system adjustment to a defect as an inspection target;

DESCRIPTION OF THE PREFERRED EMBODIMENTS

Figure 6:
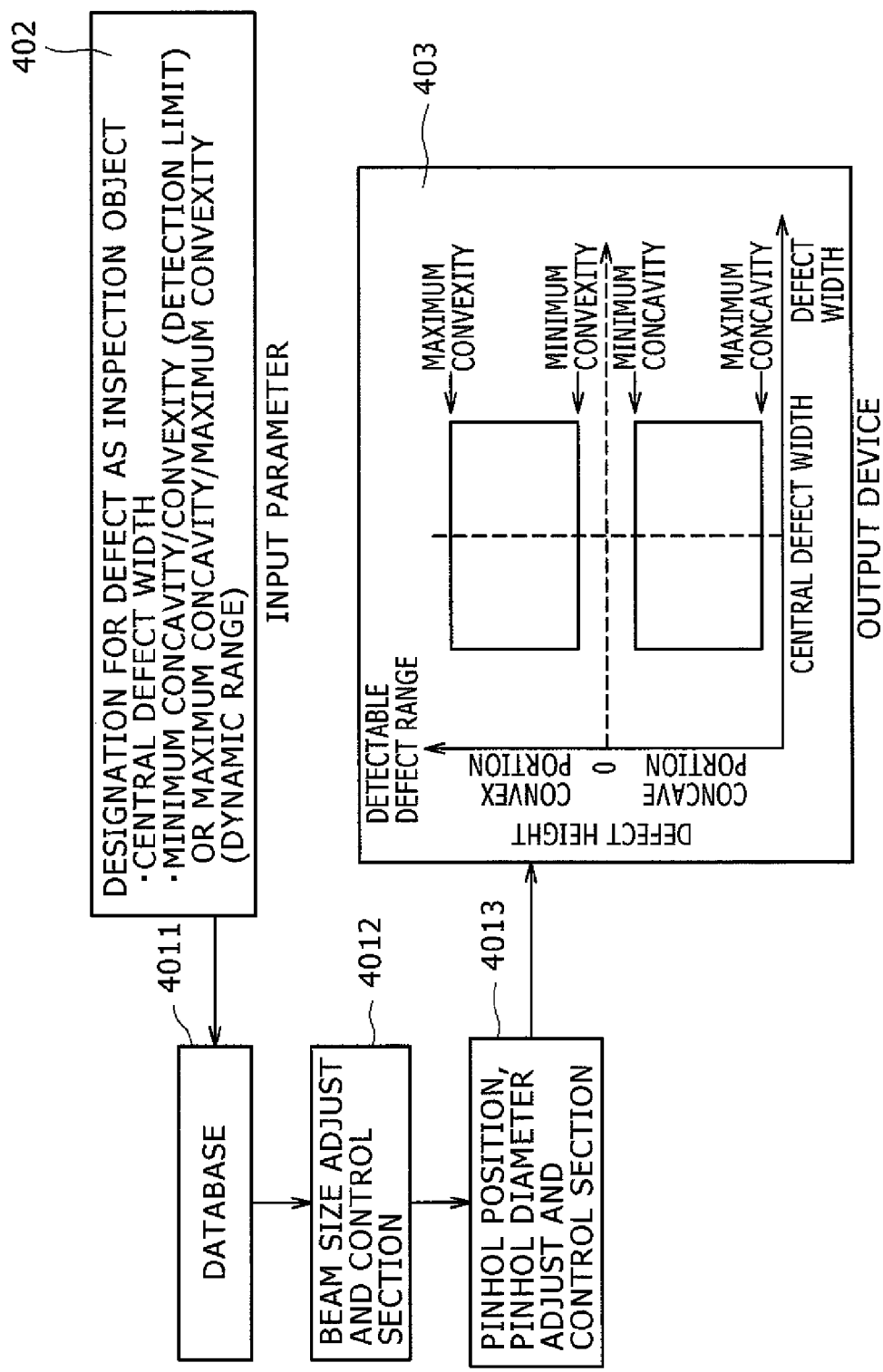
FIG. 6 is a view showing a first example of a flow chart for optical system adjustment to a defect as an inspection target according to the invention.

Preferred embodiments of a disk surface inspection method and a disk surface inspection apparatus according to the present invention are to be described with reference to the drawings.

By the way, as moderately slanted concave/convex defects present on a disk surface, those defects referred to as "wrinkle-shape" (hereinafter referred to as a wrinkle defect) are sometimes generated in addition to the convex defect (bump) and the concave defect (dimple) described above. The wrinkle defect is a defect that occurs in the heat shrinking process of a disk during manufacture thereof. FIGS. 2A to 2G show the feature for the shape of defects. FIG. 2A shows an entire disk surface, and FIGS. 2B, 2C, and 2D show enlarged views for portions α, β, and γ where bump, dimple, and wrinkle defects occur respectively. The cross sectional profile for FIG. 2B is shown in FIG. 2E, the cross sectional profile for FIG. 2C is shown in FIG. 2F, and the cross sectional profile for FIG. 2D is shown in FIG. 2G, respectively. The concave/convex defect has a shape similar to that of a Gaussian distribution, and the wrinkle defect is a defect where linear or arcuate concavity/convexity occurs periodically. As the reason that such concavity/convexity on the surface may cause the defect, in case of HDD, since the height of the concave/convex defect is larger than the head flying height, (distance between the head and the disk), this may cause crushing to a head or cause a non-tracking state to the head. Further, while the wrinkle defect height is less than the head flying height, if such a defect is present on the disk surface, the flying height of the head is not stable and causes an undesired effect on the accuracy of magnetic reading and writing.

First Embodiment

A first embodiment of the invention is to be described in detail. FIG. 1 is a schematic entire configurational view showing a first embodiment of a disk surface inspection apparatus according to the present invention. The disk surface inspection apparatus according to the invention includes an optical system (101 to 114) and an optical system (201 to 206) of a dual system having projection optical systems 100, 200 and receiving optical systems 120, 210 respectively, in which the projection optical systems 100, 200 and the receiving optical system 120, 210 are arranged at predetermined positions so that plural defects on the surface of a disk 301 can be detected. In the first embodiment, the first projection optical system 100 and the first receiving optical system 120 detect minute defects such as "pit", "handling damage", "stain", "particle", and "scratch", respectively, and the second projection systems 200 and the second receiving optical system 210 detect smooth surface concavity/convexity such as "bump", "dimple", and "wrinkle" defects, respectively. As described above, the apparatus includes plural optical systems corresponding to the kinds of the defects.

The first projection optical system 100 includes, for example, a first projection device 101 for emitting a laser beam and a first beam spot diameter adjusting mechanism 102 so as to project a laser beam by forming finely concentrated beam spot diameter 116 to the surface of the disk 301, in order to be capable of detecting a minute defect. The second projection optical system 200 includes, for example, a second projection device 201 for emitting a laser beam and a second beam spot diameter adjusting mechanism 202 so as to project a parallel light having a predetermined width (for example, parallel laser beam) capable of inspecting the defect on the surface of the disk 301 such that a smooth surface concavity/convexity can be detected. Identical positions on the surface of the disk 301 on which beams of a dual system are projected are scanned, for example, spirally by a stage 302.

In case a defect is present on the surface of the disk 301, the beam spot projected on the surface is scattered and the receiving optical systems 120, 210 receive the scattered light to obtain plural defect data signals. More specifically, among the reflection light from the surface of the disk 301 caused by the projection of the finely concentrated beam spot 116 projected by the first projection optical system 100, a bright field component of the reflection light (component approximate to 0 order diffraction light) is condensed by a condensing lens 106, branched at a branching optical system 107, and filtered by a filter 108 that shuts a normal reflection light component and transmits the scattered light component among the bright field component of the reflection light and received by a first photoreceiving device 115.

On the other hand, a dark view field component of the reflection light (high order diffraction light component) is received by second photoreceiving devices 104 and 105 (in which a dark view field component scattered from the disk surface in the direction of a lower angle is received by the photoreceiving device 105, while the dark view field component scattered in the direction of a higher angle is received by the photoreceiving device 104).

Then, in the reflection light from the surface of the disk 301 caused by the projection of the beam spot 116 from the first projection optical system 100, the normal reflection light branched at the branching optical system 107 is received by the photoreceiving device 103, and the normal reflection light from the surface of the disk 301 caused by the projection of a parallel light 207 having a predetermined width from the second projection optical system 200 is received by a photoreceiving device 208.

When a defect is present on the surface of the disk 301, the normal reflection light is increased or decreased and received by each of the photoreceiving devices 103 and 208. As described above, each of the photoreceiving devices 103 to 105, 115, and 208 are disposed so as to receive a light corresponding to the normal reflection light and the scattered light having different light intensity depending on the type of the defect.

Further, in order that each of the photoreceiving devices 103 to 105, 115, and 208 efficiently receives light to be detected respectively (that is, normal reflection light or scattered light), devices such as the branching optical system 107, a filter 108, the filter (pinhole: diaphragm) 109 as a photoreceiving surface for receiving (transmitting) the normal direction light, a filter (pinhole: diaphragm) 203 as a light receiving surface for receiving (transmitting) the normal reflection light, and condensing lenses 106, 113, 114 are disposed in each of the optical paths. As a matter of fact, the configuration of the disk surface inspection apparatus is not restricted only to that described above.

Each of the photoreceiving devices 103 to 105, 115, and 208 outputs defect data signals by the detection of the reflection light from the surface of the disk 301 by way of an electric circuits (frequency filters 404, etc.), and inputted to a signal intensity judging section 4014 of a signal processing apparatus 401. The defect data signals obtained by the respective photoreceiving devices are subjected to coordination transformation by a coordination transformation section 4016 corresponding to predetermined unit cells on the disk surface (for example, fine square cells each defined by a fine distance $\Delta r$ in the radial direction and a fine distance $\Delta \theta$ in the circumferential direction) and stored in the address of a memory. Further, a shape-dependent defect judging section 4017 judges the defect based on the feature for the shape of the defect such as the continuity of the stored address and the density. The defect detection section 4018 outputs the result judged to be the defect from an output device (operation terminal) 403. Each of the photoreceiving devices 103 to 105, 115, and 208 is formed of a photomultiplier, etc.

By the way, moderately inclined concave/convex defect present on the surface of the disk detected by the second projection optical system 200 and the second detection system 210 may sometimes include a defect referred to as "wrinkle-shape" (hereinafter referred to as wrinkle defect) in addition to the convex defect (bump) and the concave defect (dimple) as described above. The wrinkle defect is a defect that occurs in the heat shrinking process of the disk during manufacture thereof. FIGS. 2A to 2G show the feature for the shape of the defects. FIG. 2A shows an entire disk surface, and FIGS. 2B, 2C, and 2D show enlarged views for portions $\alpha$, $\beta$, and $\gamma$ where bump, dimple, and wrinkle defects occur respectively. Further, the cross sectional profile for FIG. 2B is shown in FIG. 2E, the cross sectional profile for FIG. 2C is shown in FIG. 2F, and the cross sectional profile for FIG. 2D is shown in FIG. 2G, respectively. The concave/convex defect has a shape similar to that of a Gaussian distribution, and the wrinkle defect is a defect where linear or arcuate concavity/convexity occurs periodically. As the reason that such concavity/convexity on the surface may cause the defect, in case of hard disk drive (HDD), since the height of the concave/convex defect is larger than the head flying height, this may cause crushing to a head or cause non-tracking state to the head. Further, while the height of the wrinkle defect from the surface of the disk is less than the head flying height, if such a defect is present on the disk surface, the flying height of the head is not stable and causes an undesired effect on the accuracy of magnetic reading and writing.

A defect of a lower aspect ratio (surface concavity/convexity) is detected by the second projection optical system 200 by receiving the normal reflection light from the surface of the disk 301 projected by the parallel light 207 with the photoreceiving device 208 of the second detection system 210. The detection principle for the defect of the lower aspect ratio is to be described with reference to FIGS. 3A to 3E.

The second projection optical system 200 is configured such that a parallel light 207 having a predetermined width of such an extent as capable of detecting the defect is projected to the surface of a disk 301 and the normal reflection light from that and passed through a filter (pinhole) 203 is received by a photoreceiving device 208.

As shown in FIG. 3B, in a case where a concave defect 3011 is present on the surface of the disk 301, the concave defect 3011 acts like a convex lens and the parallel light 207 incident in the concave defect 3011 is reflected to be condensed and passing through the filter (pinhole) 203 to be received by the photoreceiving device 208. In this case, the signal level output from the photoreceiving device 208 is increased by increasing the amount of light received by the photoreceiving device 208 as shown in FIG. 3D, and the concave defect 3011 can be detected from the signal output from the photoreceiving device 208 by applying a threshold value 2083 to the signal.

Further, as shown in FIG. 3C, in a case where a convex defect 3012 is present on the surface of the disk 301, the convex defect 3012 acts like a concave lens in which the parallel light 207 incident in the convex defect 3012 is reflected to be widened and passing through the filter (pinhole) 203 to be received by the photoreceiving device 208. In this case, the signal level output from the photoreceiving device 208 is decreased by decreasing the amount of light received by the photoreceiving device 208 as shown in FIG. 3E, and the convex defect 3012 can be detected from the signal output from the photoreceiving device 208 by applying the threshold value 2084 to the signal.

As has been described above, the detection principle using the parallel light 207 for the second projection optical system 200 is explained by referring FIGS. 3A to 3E. The concave/convex defects 3011, 3012 on the surface of the disk 301 can also be detected in the same manner by using a converged light (beam spot light) 209 as shown in FIGS. 4A to 4E for the second projection optical system 200. In the case of using the converged light 209, since the light is irradiated to the surface of the disk 301 in a state where the beam has already been diverged, the way of adjusting the optical system is different from that for the optical system in FIGS. 3A to 3E.

As described above, the smooth concave/convex defect on the surface of the disk 301 can be detected by receiving the normal reflection light caused by the projection of the parallel light 207 from the second projection optical system 200 with the photoreceiving device 208 of the second detection system 210. FIGS. 5A to 5F show the result of detection for the concave/convex defect and the wrinkle defect shown in FIGS. 2A to 2G by using the optical system 200 and 210. When comparing FIGS. 2A to 2G and FIGS. 5A to 5F with each other, the relation between height for the concavity/convexity and the signal intensity for the concavity/convexity are inverted. This is because the concave defect increases the signal intensity and the convex defect decreases the signal intensity as shown by the detection principle in FIGS. 3A to 3E. However, the width and the period of the detection signal are identical with those of the original defect shape.

Next, an embodiment for the sensitivity adjustment conducted by the signal processing apparatus 401 shown in FIG. 1 as the feature of the invention is to be described. That is, the first projection optical system 100 includes the first beam spot diameter adjusting mechanism 102 for adjusting the beam spot diameter, and the first detection system 120 includes the first pinhole position adjusting mechanism 110 for adjusting the position of the pinhole 109 in the direction of the optical axis and a first pinhole diameter adjusting mechanism 112 for adjusting the pinhole diameter of the pinhole 109. In the same manner, the second projection optical system 200 includes a second beam spot diameter adjusting mechanism 202 for adjusting the beam spot diameter and the second detection system 210 includes a second pinhole position adjusting mechanism 204 for adjusting the position of the pinhole 203 in the direction of the optical axis and a second pinhole diameter adjusting mechanism 206 for adjusting the pinhole diameter of the pinhole 203. Further, the first and the second pinhole diameter adjusting mechanisms 102 and 202 are adjusted and controlled by a beam size adjusting and controlling section 4012 of a signal processing device 401. The first and the second pinhole position adjusting mechanisms 110 and 204, and the first and the second pinhole diameter adjusting mechanisms 112 and 206 are adjusted and controlled by the pinhole position/pinhole diameter adjusting and controlling section 4013 of the signal processing device 401. Further, the above mechanisms 102, 202, 110, 112, 204, and 206 can be adjusted automatically by inputting signals from an operation screen such as GUI of an operation terminal 403.

The sensitivity adjustment according to the first example of the invention is explained by referring the data flow shown in FIG. 6. The data base 4011 stores information of a relationship between the shape of the defects as the inspection targets existing on the disk 301 and the arrangement of the optical system for having sufficient sensitivity for the detection of defects having the shape (projection optical systems 100, 200 and receiving optical systems 120, 210) which is obtained by simulation or experiment. Accordingly, when the shape information of the defect (central defect width: minimum concavity/convexity (detection limit), or maximum concavity/maximum convexity (dynamic range)) 402 is inputted, the beam size adjusting and controlling section 4012 automatically controls the first beam spot diameter adjusting mechanism 102 and the second beam spot diameter adjusting mechanism 202 so as to attain an optimal beam spot diameter based on the stored data base 4011, and the pinhole position/pinhole diameter adjusting and controlling section 4013 automatically controls the first and the second pinhole adjusting mechanisms 110, 204 so as to attain the optimal pinhole position in the direction of the optical axis and the section 4013 automatically controls the first and the second pinhole diameter adjusting mechanisms 112, 206 so as to attain the optimal pinhole diameter. When the sensitivity adjustment has been completed, a detectable range for the defect shape is displayed based on the inputted defect shape on the output device (operation terminal) 403. As an example, by inputting a central defect width, a detectable range for defect shape is decided and, in a case of designating the minimum concave value and the minimum convex value (detection limit), the detectable range for the maximum concavity to maximum convexity (dynamic range) is decided by the optical arrangement automatically and, in a case of designating the maximum concavity to maximum convexity range (dynamic range), the minimum concave value and the minimum convex value detection limit) are decided automatically.

Figure 7:
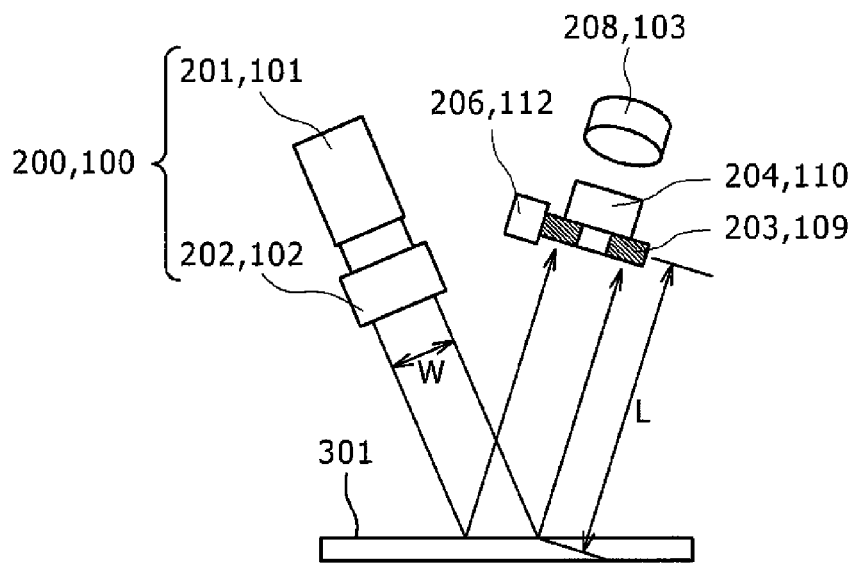
FIG. 7 is a view showing an embodiment of an optical system according to the invention.
Figure 8A:
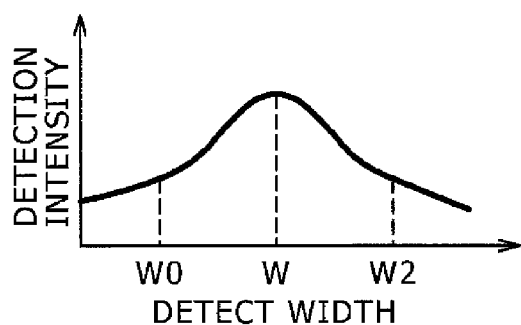
FIG. 8A is a view showing a relation between a defect width and a beam spot diameter.
Figures 8B, 8C, 8D:
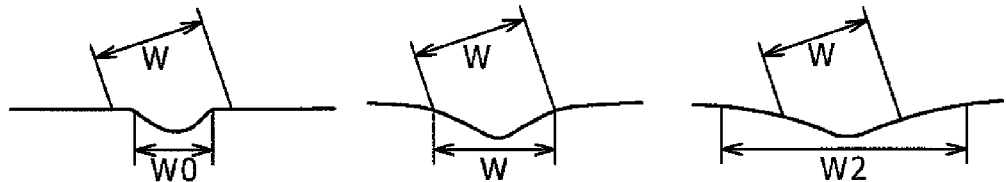
FIG. 8B is a view showing a state where a defect width W0 is smaller than a beam spot diameter W.
FIG. 8C is a view showing a state where the beam spot diameter W and the defect width W are substantially identical.
FIG. 8D is a view showing a state where the defects width W2 is larger than a beam spot diameter W.

Then, the relation between the defect shape, and the beam spot diameter, the pinhole position, and the output signal in the sensitivity adjustment applicable to the first optical systems 100 and 120 or the second optical systems 200 and 210 according to the invention is to be described by referring to FIG. 7. The beam spot diameter W of the parallel lights 207, 116 projected to the surface of the disk 301 can be changed and adjusted automatically by using the beam spot diameter adjusting mechanisms 202, 102 controlled by the beam size adjusting and controlling section 4012. Further, the position (distance) L for the pinholes 203, 109 in the direction of the optical axis can be changed and adjusted automatically by using the pinhole position adjusting mechanisms 204, 110 controlled by the pinhole diameter adjusting and controlling section 4013. FIG. 8A shows a relation between the defect width and the detection intensity. FIG. 8B shows a case where the defect width W0 is smaller than the beam spot diameter W, FIG. 8C shows a case where the beam spot diameter W and the defect width W are substantially identical, and FIG. 8D shows a case where the defect width W2 is larger than the beam spot diameter W. By aligning the beam spot diameter to a width of a defect of interest, the defect detection sensitivity can be adjusted to the defect. While the light condensing property is best when the defect width and the beam spot diameter are substantially identical, light from a defect having a width somewhat deviated from the beam spot diameter can be detected since the light reflected from the defect is also condensed. So, the detectable defect size to an arbitral beam spot size has a range.

Figure 9A:
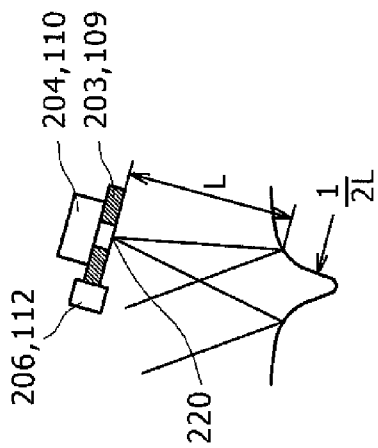
FIG. 9A is a view showing a relation between the radius of curvature at the defect top (=height) and the detection intensity detected by a detector when detected by an optical system having the configuration shown in FIG. 7.
Figure 9B:
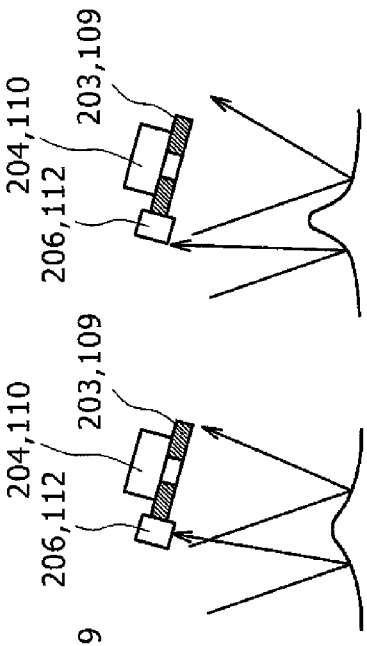
FIG. 9B is a view showing a positional relation between the incident light/reflection light to a concave defect of a large negative radius of curvature and a pinhole of the optical system having the configuration shown in FIG. 7.
Figures 9C, 9D, 9E:
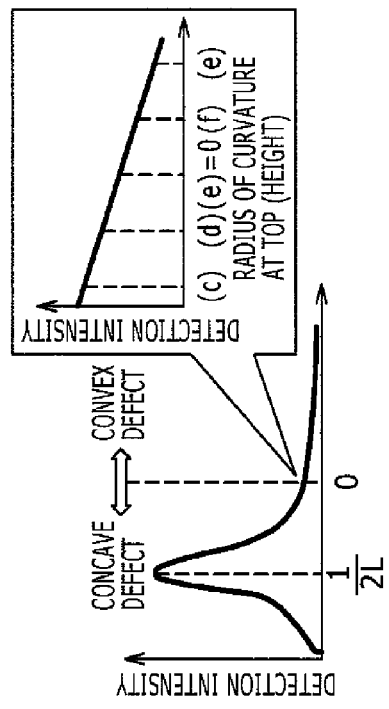
FIG. 9C is a view showing a positional relation between the incident light/reflection light to a concave defect of a medium negative radius of curvature and a pinhole of the optical system having the configuration shown, in FIG. 7.
FIG. 9D is a view showing a positional relation between the incident light/reflection light to a concave defect of a small negative radius of curvature and a pinhole of the optical system having the configuration shown in FIG. 7.
FIG. 9E is a view showing a positional relation between the incident light/reflection light to a defect-free region of radius of curvature of 0 and a pinhole of the optical system having the configuration shown in FIG. 7.
Figures 9F, 9G:
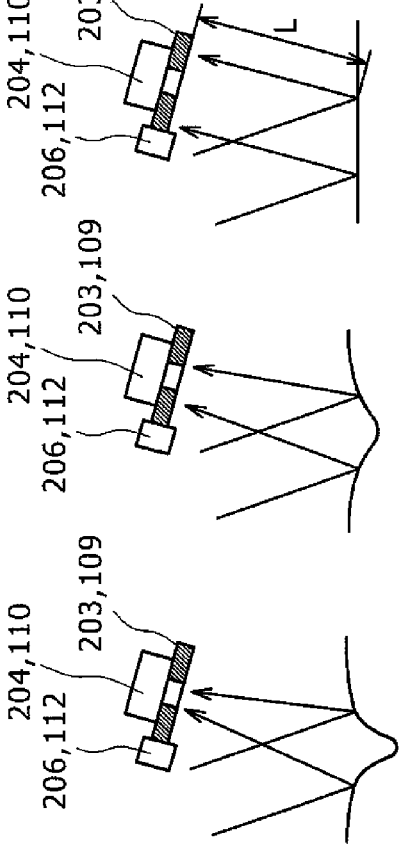
FIG. 9F is a view showing a positional relation between the incident light/reflection light to a concave defect of a small positive radius of curvature and a pinhole of the optical system having the configuration shown in FIG. 7.
FIG. 9G is a view showing a positional relation between the incident light/reflection light to a concave defect of a large positive radius of curvature and a pinhole of the optical system having the configuration shown in FIG. 7.

Then, FIGS. 9A to 9G show a relation between the defect height and the pinhole position. FIG. 9A shows a relation between the radius of curvature at the defect top (=height) and the detection intensity. The radius of curvature 0 shown in FIG. 9E shows a defect free state, positive radii of curvature shown in FIGS. 9F and G show convex defects and negative radii of curvature shown in FIGS. 9B to D show concave defects. From the light convergence and divergence characteristics of the optical system, the defect radius of curvature and the detection intensity are in an inverse proportion relation, which means the detection intensity decreases at the convex portion and the detection intensity increases at the concave portion. The detection intensity is a maximal value at the point of radius curvature of $1/(2L)$. The point for the radius of curvature of $1/(2L)$ provides a radius of curvature where the light condensation point 220 situates at the pinhole position. When the radius of curvature of a defect increases more toward the negative region, the light beam reflected from the defect is once condensed and then diverged at the pinhole position, and the detection intensity decreases.

In the measurement for the concave/convex defect at the disk surface according to the invention, the optical system is designed such that the range for the height of the concave/convex defect to be measured is contained in a region near the height of 0. It has been known that a linear response is obtained in this region as shown by the solid line in the enlarged view of FIG. 9A. That is, the height of the concave/convex defect and the detection intensity have a linear relation as shown in FIGS. 9C to 9G.

Figure 10A:
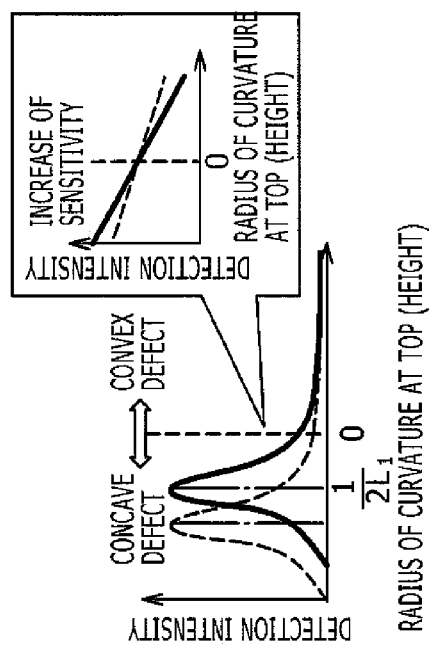
FIG. 10A is a view showing a positional relation between an irradiation optical system, and a pinhole and a detector in a state of spacing apart the position of the pinhole from the disk surface further relative to a reference distance L in FIG. 7 in the direction of the optical axis.
Figure 10B:
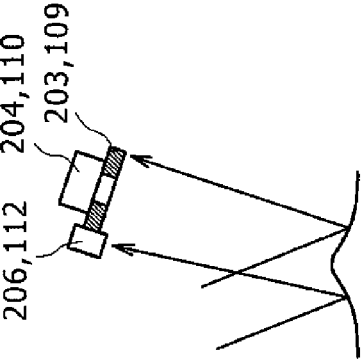
FIG. 10B is a graph showing a relation between the radius of curvature at a defect top and a detection intensity detected by the detector in a case of using the optical system having the configuration shown in FIG. 10A.
Figure 10C:
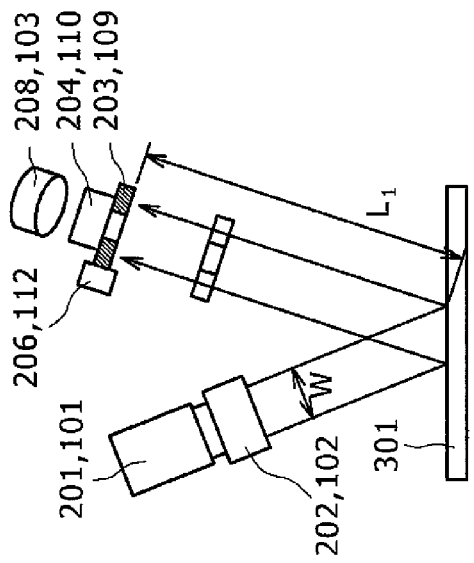
FIG. 10C is a view showing a positional relation between the incident light/reflection light to a concave defect and the pinhole of the optical system having the configuration shown in FIG. 10A.
Figure 10D:
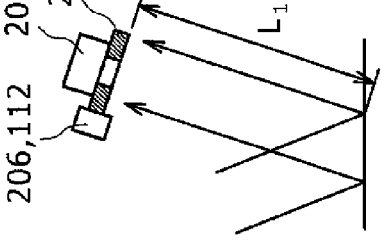
FIG. 10D is a view showing a positional relation between the incident light and reflection light to a defect free region and the pinhole of the optical system having the configuration shown in FIG. 10A.
Figure 10E:
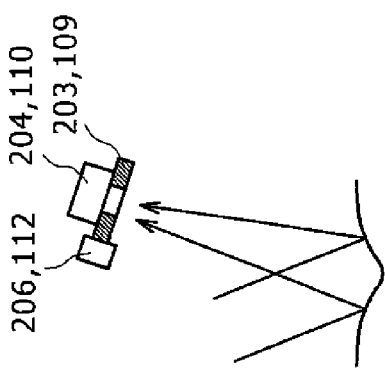
FIG. 10E is a view showing a positional relation between the incident light/reflection light to a convex defect and the pinhole of the optical system having the configuration shown in FIG. 10A.

Then, the sensitivity adjustment due to the change of the pinhole position is explained. FIG. 10A shows a state that a distance between the surface of the disk 301 and the pinhole 203 or 109 in the direction of the optical axis is $L_1$ which is greater the distance L in FIG. 7 (the radius of curvature $1/(2L)$ is such a radius of curvature that the condensation point 220 is at a pinhole position as shown in FIG. 9B). In this case, since the point for the radius of curvature $1/(2L_1)$ for the maximal value approaches 0 as shown in FIG. 10B, the sensitivity becomes higher where the radius of curvature at the top (height) is in the vicinity of 0 as shown by the solid line in an enlarged view of FIG. 10B (The doted curve or line in FIG. 10B corresponds to the solid curve or line shown in FIG. 9A). This corresponds to that even a slight change in height of concave/convex defect can be recognized as a large intensity change by enlarging the distance $L_1$ between the pinhole 203 or 109 and the surface of the disk 301 as compared to L in the direction of the optical axis, as shown in FIGS. 10C to 10E. In this case, however, there is a disadvantage that the detectable range for the maximum concavity to maximum convexity (dynamic range) is narrowed.

Further, FIG. 11A shows a state that a distance between the surface of the disk 301 and the pinhole 203 or 109 in the direction of the optical axis is $L_2$ which is smaller the distance L in FIG. 7. In this case, since the point for the radius of curvature $1/(2L_2)$ of the maximal value is away from 0 as shown in FIG. 11B solid curve, the sensitivity lowers in the vicinity of 0 for the radius of curvature at the top (height) as shown by the solid line in the enlarged view of FIG. 11B (The doted curve or line in FIG. 11B correspond to the solid curve or line in FIG. 9A). This means that by decreasing the distance $L_2$ between the pinhole 203, 109 and the surface of the disk 304 relative to the reference distance L thereby extending the dynamic range, even a large change in height of concave/convex defect can be detected. In this case, however, there is a disadvantage that a slight change in height of concave/convex defect cannot be detected in a case of using a sensor at an identical noise level in the case of in FIG. 9.

As has been described above, by increasing the distance $L_1$ or decreasing the distance $L_2$ by changing the position of the pinhole 203 or 109 relative to the reference distance L in the direction of the optical axis, it is possible to make the sensitivity higher thereby detecting smaller concave/convex defect or extend the dynamic range wider thereby detecting larger concave/convex defect.

Then, the relation between the defect shape, and the beam spot diameter and the pinhole position of an optical system which condenses the illumination light before illuminating the light to the disk surface is explained. This optical system can be applied to the first optical system 100 and 120 or the second optical system 200 and 210 according to the invention with reference to FIG. 12. The beam spot diameter W and the position L for the pinhole 203 or 109 (or distance L between the surface of the disk 304 and the pinhole 203 or 109) can be changed automatically by using a beam spot diameter adjusting mechanism 202, 102 and the pin hole position adjusting mechanism 204, 110. FIGS. 13A, 13B, 13C, and 13D show the relation for the defect width W0, W, W2, the distance F from the disk surface to the condensation point, and the beam spot diameter W. The sensitivity of the first optical system 100 and 120 or the second optical system 200 and 210 can be adjusted by aligning the beam spot diameter W to the defect width W0, W, W2 by changing the distance F from the disk surface to the condensation point of light emitted from the first of second projection device 101 or 201.

Then, a relation between the defect height and the pinhole position according to the invention is shown in FIGS. 14A to 14G. FIGS. 14A to 14G show a relation between the radius of curvature at the defect top (=height) and the detection intensity. Different from the case of illuminating the parallel light in FIGS. 9A to 9G, the intensity reaches a maximal value at the radius of curvature $(1/(2L))+(1/(2F))$. Since the disk surface is irradiated with the diverging light as shown in FIG. 14B, a radius of curvature of the optical system is a combination of the radius of curvature $1/(2F)$ from the focal position and the original radius of curvature $\frac{1}{2}(L)$. Further, in the vicinity of the height of 0, the change in height of the concave/convex defects and the change in the detection intensity can be regarded to have a linear relation as shown by the solid lint in the enlarged view of FIG. 14A, and in FIGS. 14C to 14G.

Figure 15A:
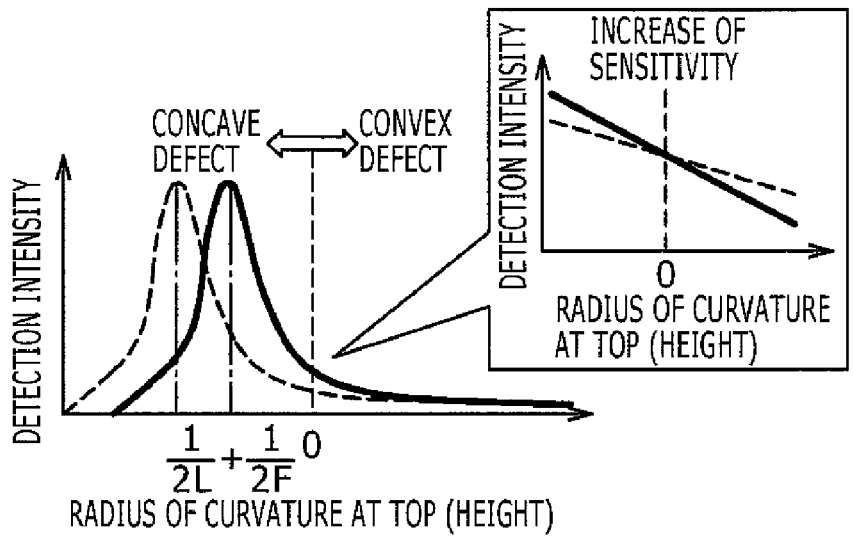
FIG. 15A is a graph showing a relation between the radius of curvature at a defect top and the detection intensity detected by the detector in a state of spacing apart the position $L_1$ of the pinhole from the disk surface further relative to a reference distance L in FIG. 12 in the direction of the optical axis.
Figure 15B:
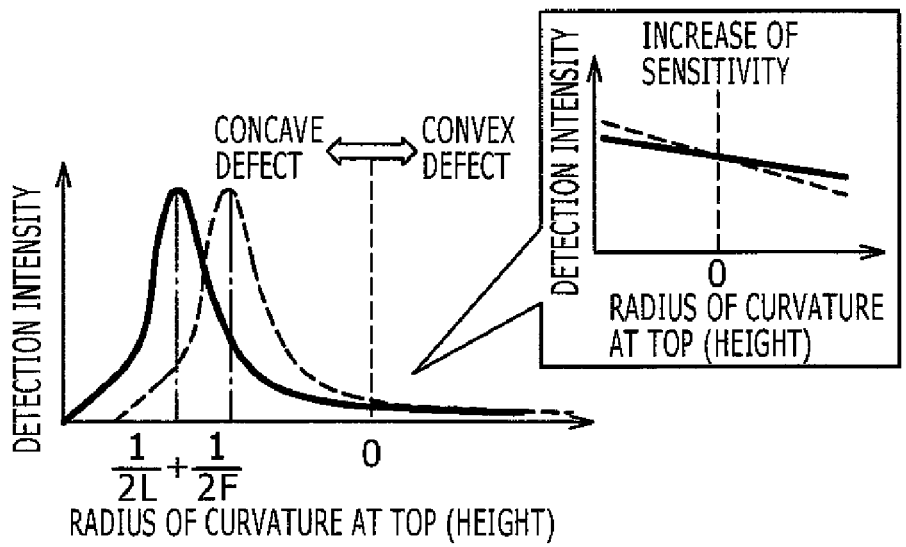
FIG. 15B is a graph showing a relation between the radius of curvature at a defect top and the detection intensity detected by the detector in a state of approaching the position $L_2$ of the pinhole to the disk surface further relative to a reference distance L in FIG. 12 in the direction of the optical axis.

Then, the sensitivity adjustment due to the pinhole position change is explained. FIG. 15A shows a state of enlarging the distance $L_1$ between the pinhole 203 or 109 and the surface of the disk 304 relative to the reference distance L in FIG. 12 in the direction of the optical axis ($L<L_1$). Since F is a fixed value upon deciding the beam spot diameter W, the sensitivity is adjusted only by the position $L_1$ for the pinhole 203 or 109 in the direction of the optical axis. In this case, since the maximal value of the solid curve, which relates to this case, is near to 0 comparing to the doted curve, which relates to the case as explained in FIG. 9, the sensitivity is higher in the vicinity of 0 as shown by the solid line in the enlarged view of FIG. 15A. On the other hand, FIG. 15B shows a state of decreasing the distance $L_2$ between the pinhole 203 or 109 and the surface of the disk 304 relative to the reference distance L in FIG. 12 in the direction of the optical axis ($L<L_2$). In this case, since the maximal value is away from 0 as shown in FIG. 15B, the sensitivity lowers in the vicinity of 0 as shown by the solid line in the enlarged view of FIG. 15B (The doted curve or line in FIG. 15B correspond to the solid curve or line in FIG. 9A).

Then, the effect of the pinhole diameter on the sensitivity in the invention is to be described with reference to FIGS. 16A to 16E. The pinhole diameter in FIG. 16A is defined as a reference size. The pinhole size is adjusted by using the pinhole diameter adjusting mechanism 206 or 112. FIG. 16B shows a case where the pinhole diameter is smaller than the reference size, and FIG. 16C shows a case where the pinhole diameter is larger than the reference size. FIG. 16D shows the sensitivity response relative to FIG. 16B. FIG. 16E shows the sensitivity response relative to FIG. 16C. In a case where the pinhole diameter is smaller than the reference size as shown in FIG. 16D, the sensitivity near the condensation point becomes abrupt. Accordingly, the sensitivity near the condensation point is at high sensitivity as shown by the solid line shown in the graph on the left below in FIG. 16D and the sensitivity at the point remote from the condensation point is at low sensitivity as shown in the graph on the right side below in FIG. 16D. On the other hand, in a case where the pinhole diameter is larger than the reference size as shown in FIG. 16E, change in the detection intensity against the change of radius of curvature at top in the vicinity of the condensation point is lower than the sensitivity of the standard pinhole size case (doted line). Accordingly, the sensitivity near the condensation point becomes lower comparing to the standard pinhole size case (doted line) as shown in the graph on the left side below in FIG. 16E and the sensitivity at the point remote from the condensation point becomes higher comparing to the standard pinhole size case (doted line) as shown in the graph on the right side below in FIG. 16E.

As has been described above, in the disk surface inspection apparatus according to the invention, it is possible to adjust the sensitivity relative to the defect width by adjusting the beam spot diameter of the optical system, and adjusting the sensitivity to the defect height by adjusting the pin hole position and the pinhole diameter, thereby adjusting the sensitivity to the defect having an optional shape.

Further, by adjusting the pinhole position and the pinhole diameter simultaneously, the movable range for the adjustment can be made smaller and a wide sensitivity adjustment is possible.

Second Embodiment

Then, description is to be made for the method of preparing a data base for the defect of an optional shape and arrangement of the optical system adjusted for the sensitivity with respect to the shape used in a disk surface inspection apparatus as a second embodiment according to the invention. The method of preparing the data base is classified into two methods, that is, (1) preparation by using optical simulation and (2) preparation based on experiment.

Figure 17A:
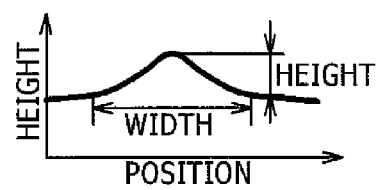
FIG. 17A is a view showing the shape of a concave defect.
Figure 17B:
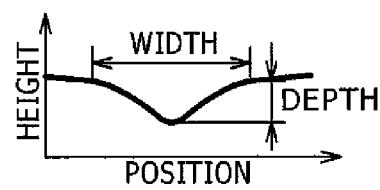
FIG. 17B is a view showing the shape of a convex defect.
Figure 17C:
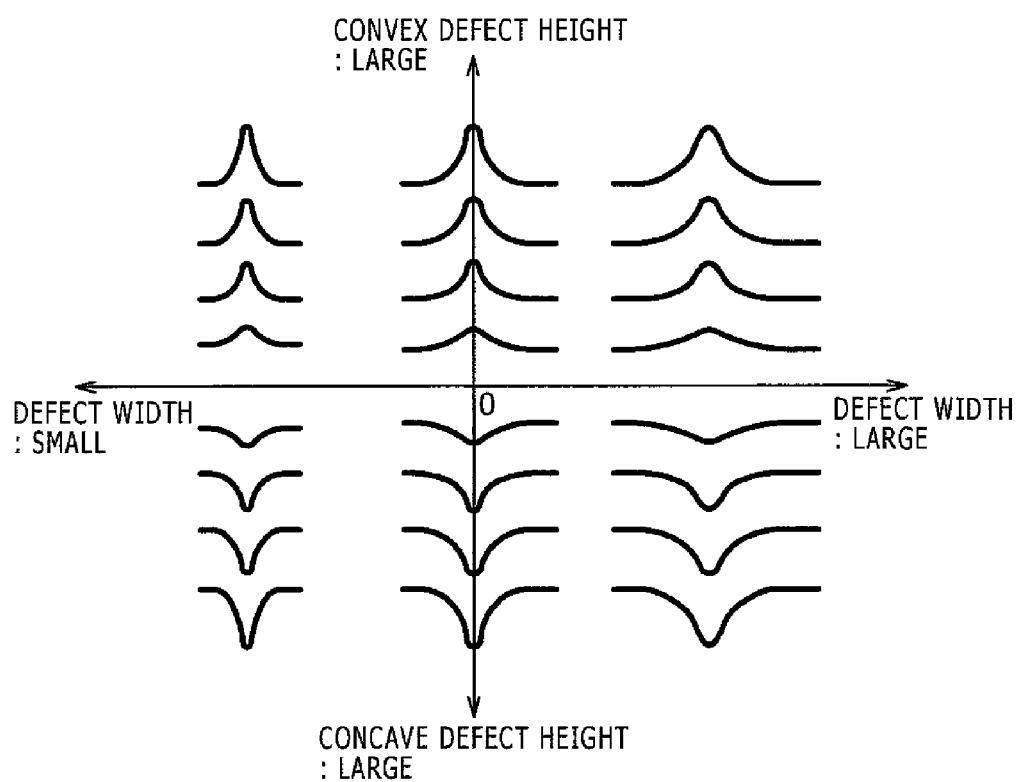
FIG. 17C is a view showing an optical simulation model in which the width and the height or the depth of the concave/convex defect shape are changed.
Figure 18B:
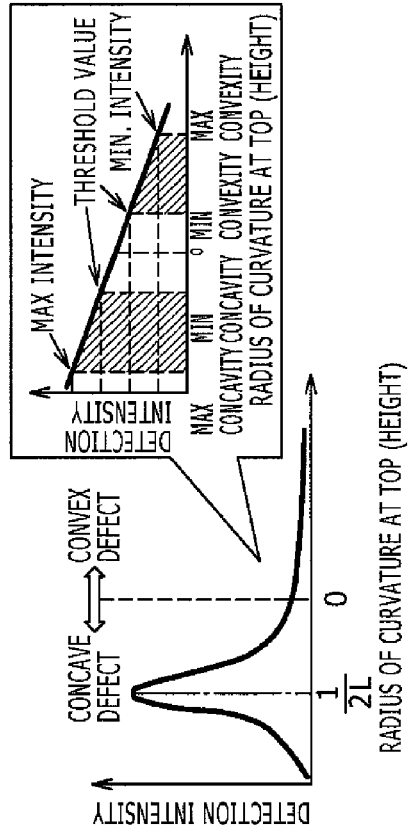
FIG. 18B is a graph showing a relation between the radius of curvature at a top of a defect determined by the optical simulation and the detection intensity.
Figure 18C:
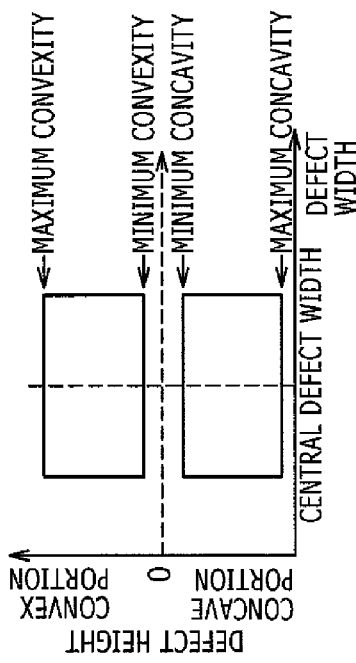
FIG. 18C is a graph showing a detectable defect range with respect to the defect width and the defect height in an arrangement of optical system in optical simulation.
Figure 18A:
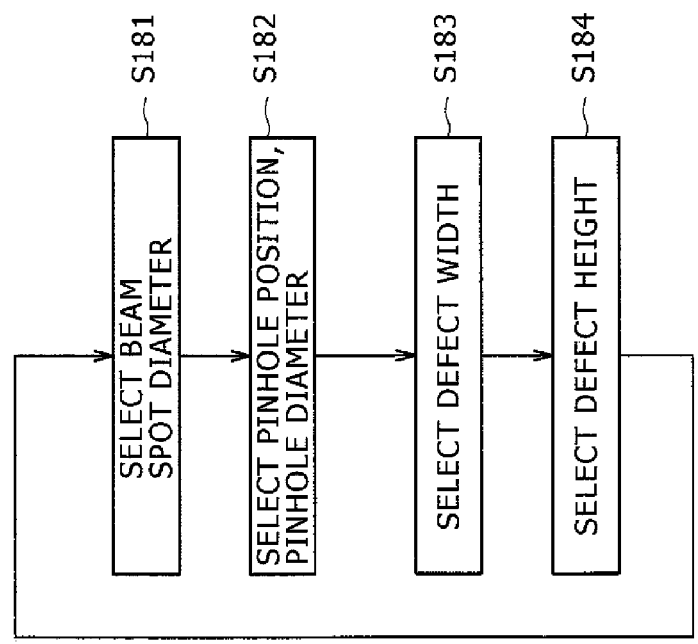
FIG. 18A is a flow chart showing the analysis procedure of optical simulation.

At first, (1) a method of preparing the data base by the optical simulation is to be described. An optical simulator to be used can be realized, for example, by a light tracking simulator used for the lens design or irradiation analysis. The optical simulator is configured, for example, by connection to an operation terminal 403. A model for the optical system inputted to the optical simulator is obtained by arrangement of the optical system shown in FIG. 7 and FIG. 12 (in the relation between the beam spot diameter adjusting amount by each of the first and second projection optical systems 200, 100, the movement adjusting amount of a photoreceiving surface and the photoreception adjusting amount to the photoreceiving surface by each of the first and the second receiving optical systems 210, 120) and is arranged based on the design data for the disk surface inspection apparatus. Further, the defect model in the disk surface inputted to the optical simulator is concave/convex defects shown in FIGS. 17A, 17B as the defect model on the disk surface to be inputted to the optical simulator. As the shape distribution of the concave/convex defect, a Gauss distribution approximate to actual concave/convex defect shape is assumed for instance. The variable parameters include the defect width, the height or the depth. FIG. 17C shows a list of defect shapes when the defect width, height, and depth are changed. FIG. 18A shows a procedure for analyzing simulation by the optical simulator. The optical simulator at first selects a beam spot diameter (S181), secondly selects a pinhole position and a pinhole diameter (S182), further selects thirdly a defect of a certain width as a defect shape (S183), then, continuously changes the height of the defect having a certain width selected in the third step (S184) to determine the detection intensity obtained therein. Then, the optical simulator calculates a relation between the detection intensity and a height of a defect having a certain width by changing the height as shown in FIG. 18B. According to this analysis, the minimum concave/convex defect height (detection limit) and the maximum concave defect height to maximum convex defect height width (dynamic range) are decided. The minimum concave/convex defect height is defined by the S/N ratio and a noise signal intensity of the apparatus which is measured beforehand the calculation. Further, the maximum concave/convex defect height is decided by the dynamic range of the detector. Same analysis is conducted also in a case of changing the defect width. And a detectable range for defect regarding the defect width and the detect height in a certain optical arrangement is decided as shown in FIG. 18C. By performing the analysis described above while changing the beam spot diameter, the pinhole position, and the pinhole diameter, and then preparing a data base 4011 including them.

Figure 19A:
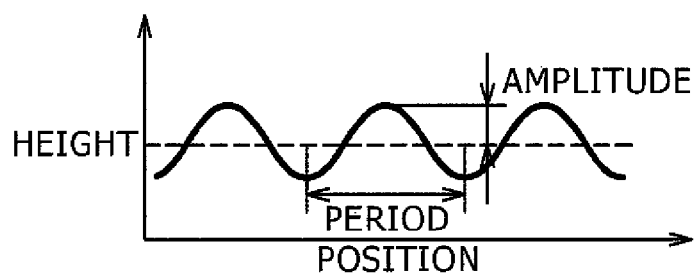
FIG. 19A is a view showing a relation between the position and the height of a shape distribution of a wrinkle defect when expressed by a sinusoidal wave.
Figure 19B:
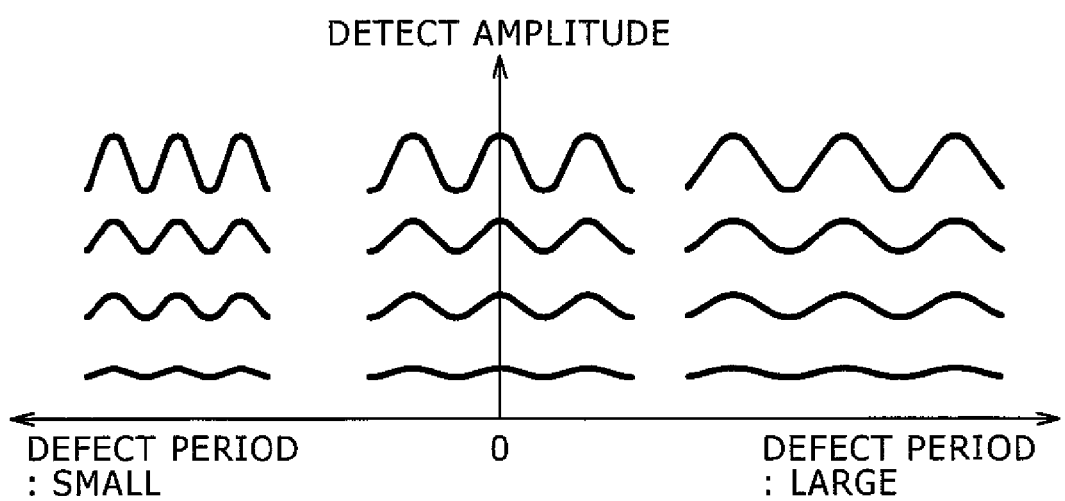
FIG. 19B is a view showing an optical simulation model in which the period and the amplitude of the shape of the wrinkle defect are changed.

Then, a case in which the defect model on the disk surface inputted to the optical simulator is a wrinkle defect is explained by referring the FIGS. 19A and 19B. As the shape distribution of the wrinkle defect, a sinusoidal wave shown in FIG. 19A which is similar to an actual defect shape is assumed as an example. The variable parameters used in the simulation include a defect period and amplitude. The optical simulator selects the beam spot diameter, the pinhole position, and the pinhole diameter in the same manner as in the analysis for the concave/convex defect and then performs simulation for the detection of defects with various periods and amplitudes shown in FIG. 19B, and decides the detectable defect width, the minimum wrinkle defect height (detection limit), and the maximum wrinkle defect height (dynamic range).

By the preparation of the data base described above, the signal processing apparatus 401 can conversely decide the arrangement for the optical system (beam spot diameter, pinhole position, and pinhole diameter) by determining the detection limit for the defect concavity/convexity upon deciding the beam spot diameter, the pinhole position, and the dynamic range, thereby inputting a defect shape information intended to be obtained by a user.

Figure 20A:
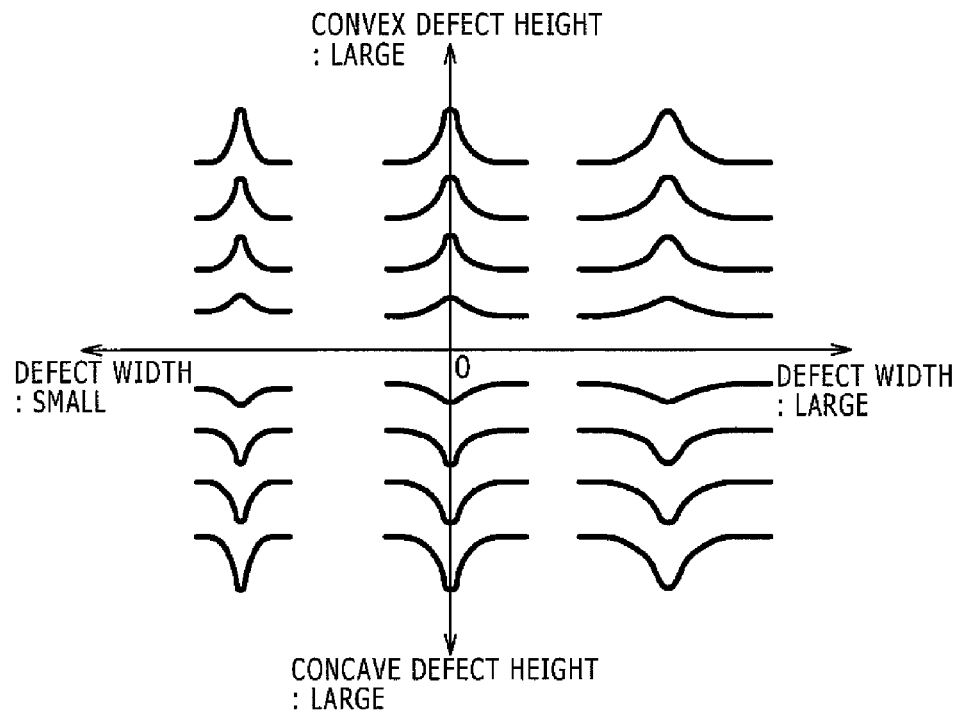
FIG. 20A is a list for defect shapes prepared by measuring the concave/convex defect shape by a three-dimensional measuring instrument.
Figure 20B:
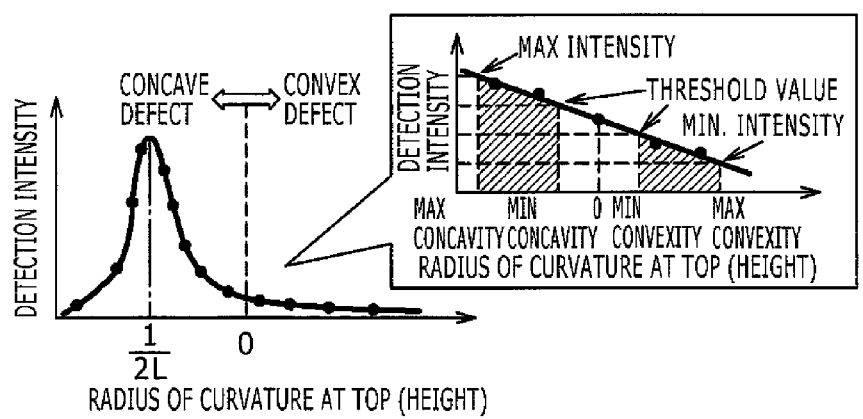
FIG. 20B is a view showing a relation between the radius of curvature at a defect top determined by a dispersive data for the concave/convex defect shape and the detection intensity.

Then, (2) a data base preparation method by using data acquired from an experimental study is to be described with reference to FIGS. 20A and 20B. For example, when plural actual defects having random shapes are available, the defect shapes are measured by a three dimensional shape measuring instrument (not illustrated) to prepare a defect shape list as shown in FIG. 20A. Then, the optical simulator selects the beam spot diameter, the pinhole position, and the pinhole diameter and decides the detection limit for the concave/convex defect height and the dynamic range in the same manner as in the simulation analysis under the conditions used therein. However, since the available defect shapes are dispersive different from those in the simulation, an approximate curve is determined, for example, by a least square method as shown in FIG. 20B to decide the detection limit for concave/convex defect height and the dynamic range based on the determined approximate curve.

Figure 21A:
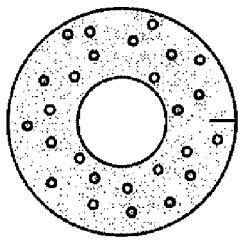
FIG. 21A is a plan view for a roughness sample A.
Figure 21B:
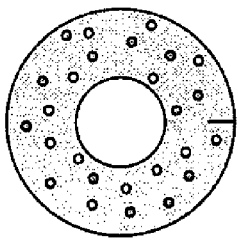
FIG. 21B is a plan view for a roughness sample B.
Figure 21C:
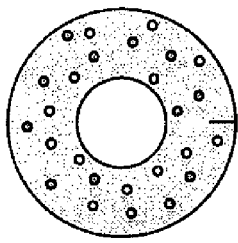
FIG. 21C is a plan view for a roughness sample C.
Figure 21D:
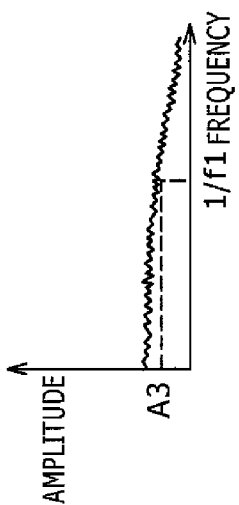
FIG. 21D is a graph showing a relation between a frequency and an amplitude prepared by conducting Fourier transformation for the data obtained by three-dimensional measurement for the surface of the roughness sample A.
Figure 21E:
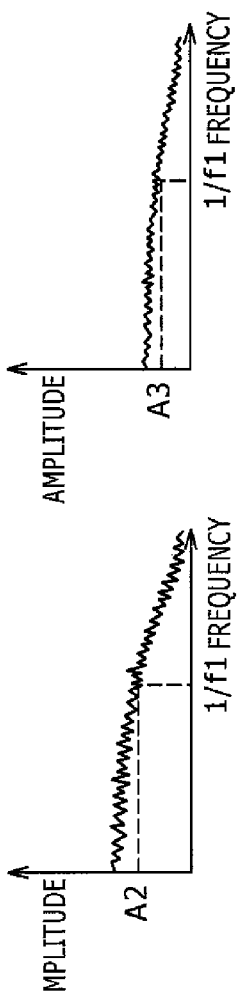
FIG. 21E is a graph showing a relation between the frequency and the amplitude prepared by conducting Fourier transformation for data obtained by three-dimensional measurement for the surface of the roughness sample B.
Figure 21F:
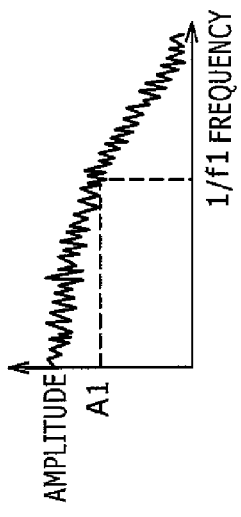
FIG. 21F is a graph showing a relation between the frequency and the amplitude prepared by conducting Fourier transformation for data obtained by three-dimensional measurement for the surface of the roughness sample C.
Figure 21G:
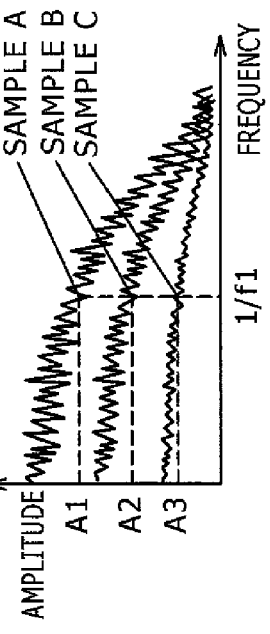
FIG. 21G is a graph expressing the graphs of FIG. 21D, FIG. 21E and FIG. 21F in juxtaposition.
Figure 22A:
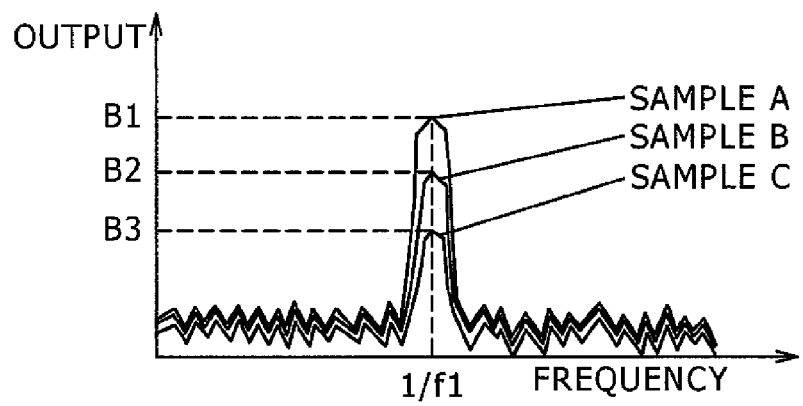
FIG. 22A is a graph showing the result of conducting Fourier transformation and frequency analysis to signals obtained by measuring the samples A, B, and C of different roughness by using, for example, the optical system as shown in FIG. 7.
Figure 22B:
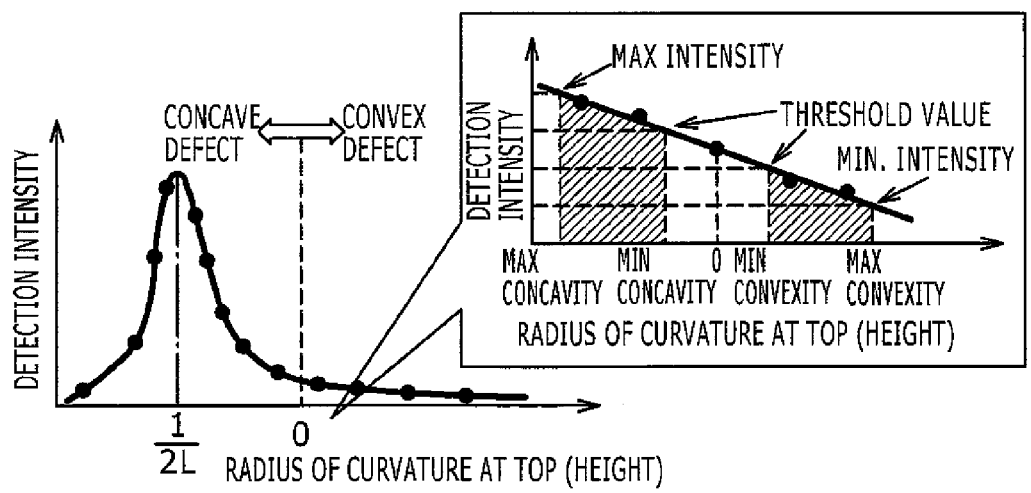
FIG. 22B is a graph showing an example of a relation between the radius of curvature at a top of defect obtained for the sample of an optional period in view of the result of FIG. 22A and the detection intensity.

In the experiment described above, it is assumed that a number of actual defect samples having random shapes are available. But, in actual, it is hard to get samples having random shapes. And there may be a possibility that the method described above cannot be applied. Then, a method shown in FIGS. 21A to 21G can be applied as a method of preparing the data base experimentally. Adjustment in this method is conducted to periodical defects (wrinkle defects). A number of samples of different surface roughness are prepared as samples to be measured. As an example; for preparing samples having different surface roughness in the disk surface polishing process, polishing the plural samples under different polishing time so as to have different surface roughness. Thus, samples of different roughness (shown in FIGS. 21A, 21B, and 21C) are prepared. Then, three-dimensional shape measurement is conducted for the samples and the measured data are subjected to Fourier transformation to determine the amplitude on every frequency component as shown in FIGS. 21D, 21E, and 21F. The frequency components are collectively shown in FIG. 21G. Accordingly, samples of different amplitudes A1, A2, A3 for an optional frequency f1 can be prepared. For the samples, the beam spot diameter, the pinhole position, and the pinhole diameter are selected in the same manner as in the simulation analysis, and the detection limit for the concave/convex defect height and the dynamic range are decided under the conditions therein. FIG. 22A is an example for the result of Fourier conversion and frequency analysis applied to output signals which are obtained when samples are measured under the conditions for a beam spot diameter, a pinhole position, and a pinhole diameter. A signal amplitude corresponding to a frequency 1/f1 shows the detection intensity for the shape of period f1. The output intensity to the sample A having the amplitude A1 is B1, the output intensity to the sample B having the amplitude A2 is B2, and the output intensity to the sample C having the amplitude A3 is B3. Then, as shown in FIG. 22B, a relation between the defect height and the detection intensity can be determined to a sample of an optional period. However, since the roughness amplitude is dispersive, an approximate curve is determined, for example, by a least square method, and the detection limit for the concave/convex defect height and the dynamic range are decided based on the determined approximate curve.

Figure 23A:
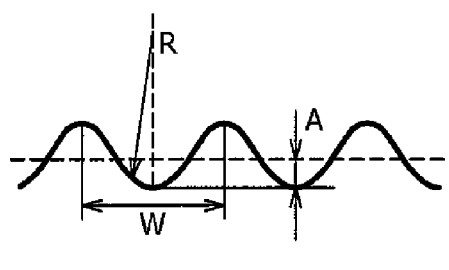
FIG. 23A is a view showing a cross sectional profile of a periodical defect.
Figure 23B:
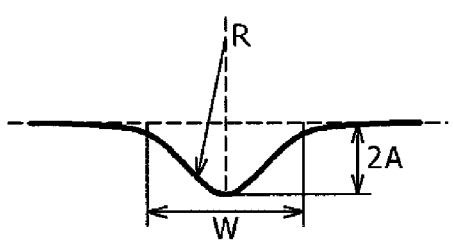
FIG. 23B is a view showing a cross sectional profile of a lone defect.
Figure 24A:
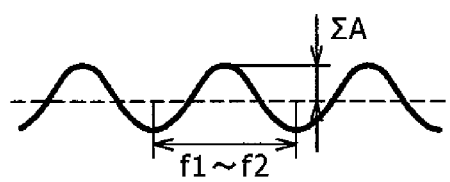
FIG. 24A is a view showing a cross sectional profile of an actual defect having several periods.
Figure 24B:
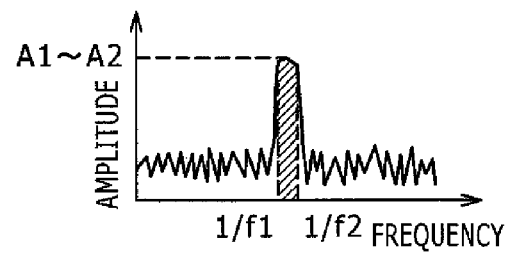
FIG. 24B is a graph showing the frequency characteristic of the surface shape of an actual defect having several periods in FIG. 24.

By using this method, it is possible to adjust a concave defect having the same radius of curvature with the periodical defect as shown in FIGS. 23A and 23B so as to have sensitivity. Accordingly, to adjust a sensitivity of the inspection apparatus to an optional concave/convex defect, it is enough to adjust the sensitivity to the periodical defect having the identical radius of curvature. Further, an actual defect is often formed not by a single period but by several periods as shown in FIGS. 24A and 24B. In this case, the amplitude has to be evaluated as a sum for the amplitudes of period contained therein. The preparation method for the data base is as has been described above.

By the method described above, a flow chart shown in FIG. 6 can be practiced. The defect shape as the inspection target is inputted by a user, for example, by using the apparatus GUI 405 shown in FIG. 25 connected to the signal processing apparatus 401. And the beam spot diameter, the pinhole position, and the pinhole diameter are adjusted automatically by the adjustment control sections 4012, 4013 based on the data base 4011 with reference to the input data. A detectable defect range 403 by the adjusted arrangement for the adjusted optical system is displayed on the apparatus screen.

Figure 26:
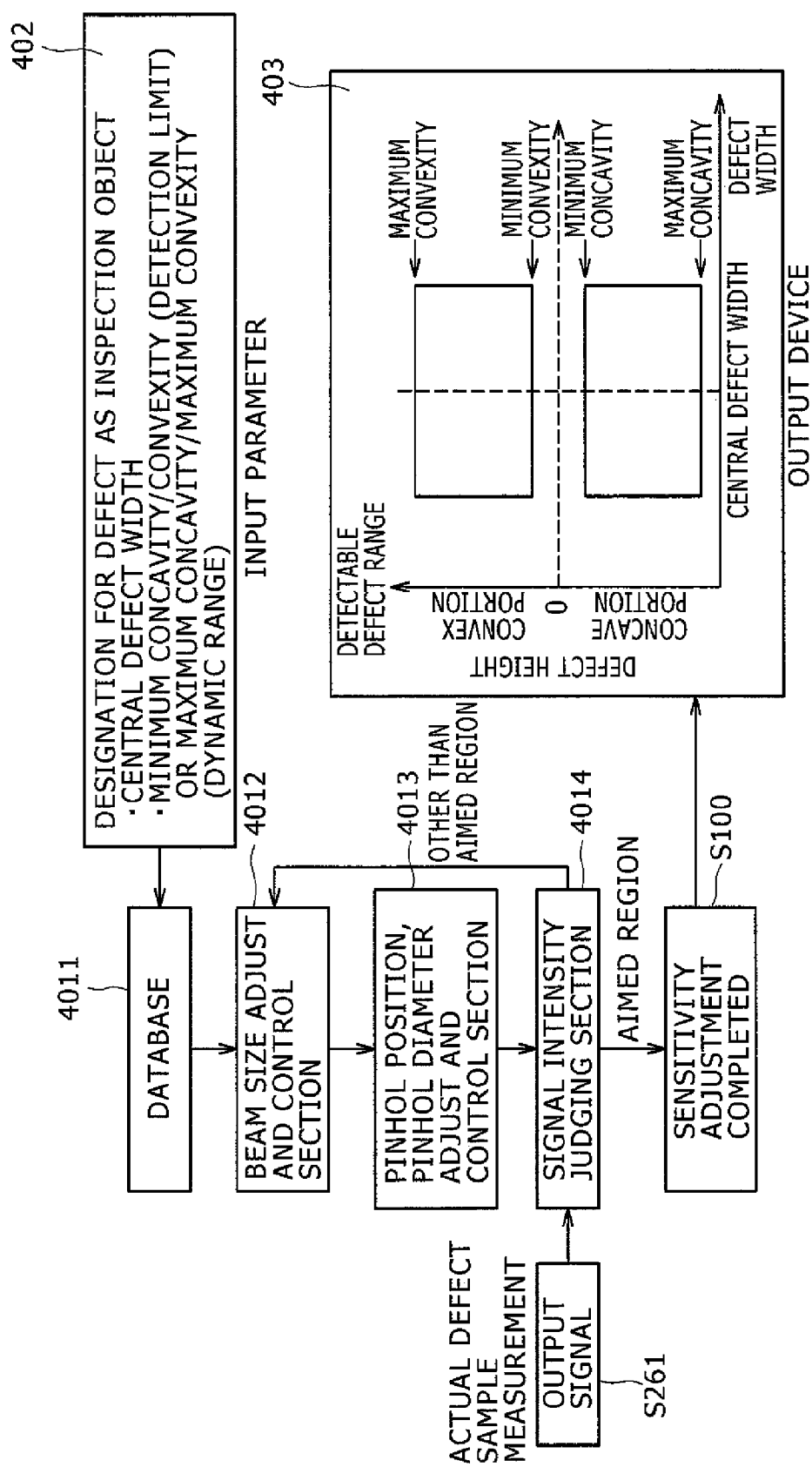
FIG. 26 is a flow chart showing a second example of a procedure for optical system adjustment to a defect as a target of inspection.

Further, FIG. 26 shows a second example of the flow chart. The process up to the designation of the defect as the inspection target (402) and automatic adjustment for the beam spot diameter, the pinhole position, and the pinhole diameter based on the data base 4011 are identical with those in FIG. 6. After the adjustment, an actual defect sample having a known shape is measured (S261). For this sample, a signal intensity obtained previously as an aimed value has been known by the data base 4011. The signal intensity judging section 4014 compares the result of measurement with the aimed value and, when the measured value is in a range near the aimed sensitivity, it is judged that the adjustment has been completed (S100). When the measured value is not in the region near the aimed sensitivity, the beam spot diameter, the pinhole position, and the pinhole diameter are finely adjusted again and adjustment is conducted till the measured result enters the aimed sensitivity region. As a result, a defect range 403 capable of detection by the arrangement for the adjusted optical system is displayed on the apparatus screen.

Figure 27:
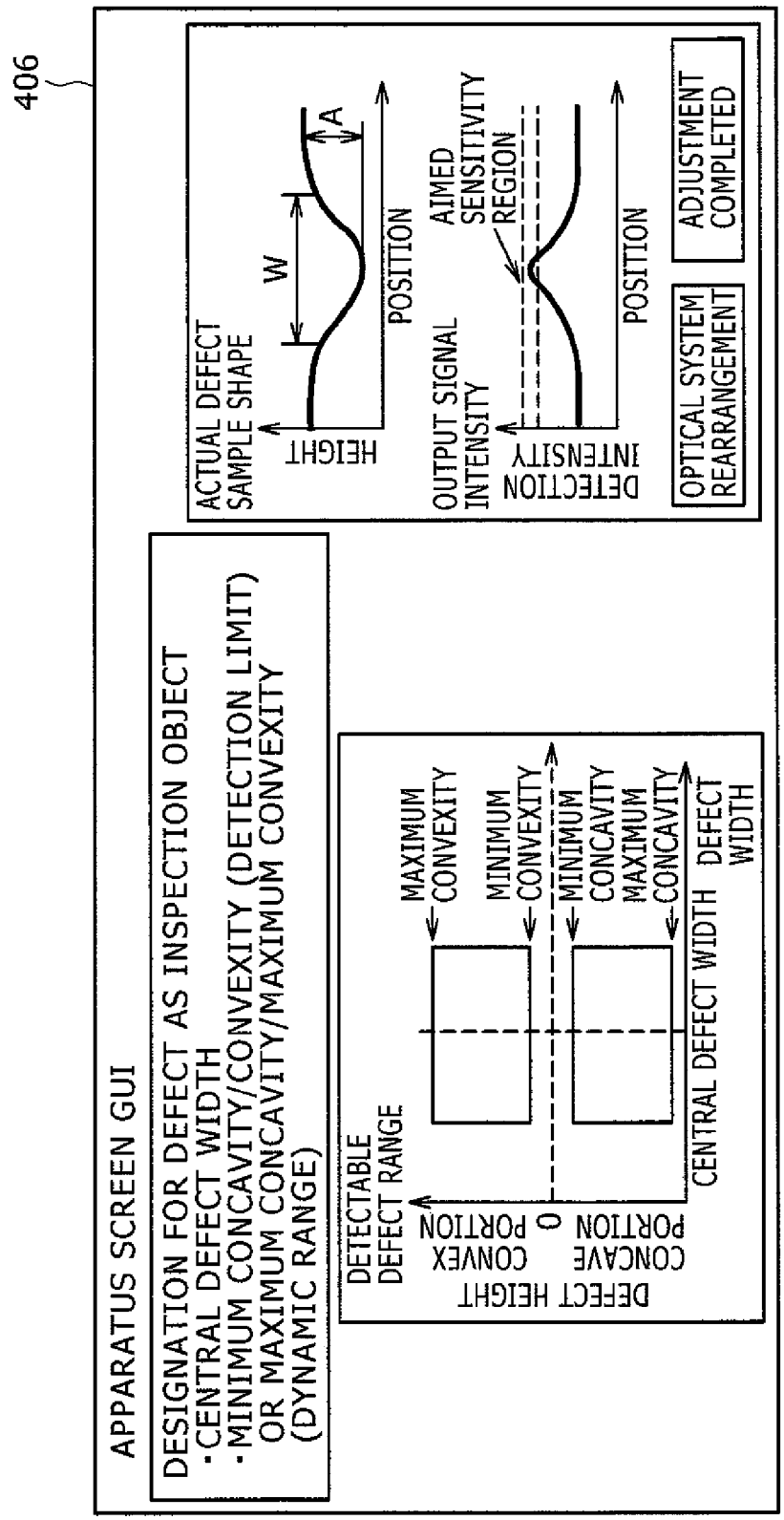
FIG. 27 is a view showing a second example of the GUI screen of the apparatus for optical system adjustment to a defect as an inspection target.

The inspection target defect data is inputted by a user, for example, by using the apparatus GUI 406 shown in FIG. 27 connected to the signal processing apparatus 401. And the beam spot diameter, the pinhole position, and the pinhole diameter are adjusted automatically by the beam size adjust and control sections 4012 and pinhole position, pinhole diameter adjust and control section 4013 based on the information stored in the data base 4011 by referring the input data. A detectable defect range is displayed on the apparatus screen 406. Further, it includes an actual sample shape input screen, and the sample shape of width W and height or depth A of the sample to be measured is inputted. Then, an aimed sensitivity region is set by the data base 4011 and the signal intensity judging section 4014 judges whether the result of measurement is in the aimed region or not. If it is not in the region, the beam spot diameter, the pinhole position, and the pinhole diameter are finely adjusted again automatically or by user's judgment by the adjusting and controlling sections 4012 and 4013. If it is in the aimed sensitivity region, it is judged that the adjustment for the optical system has been completed (S100).

Third Embodiment

Figure 28:
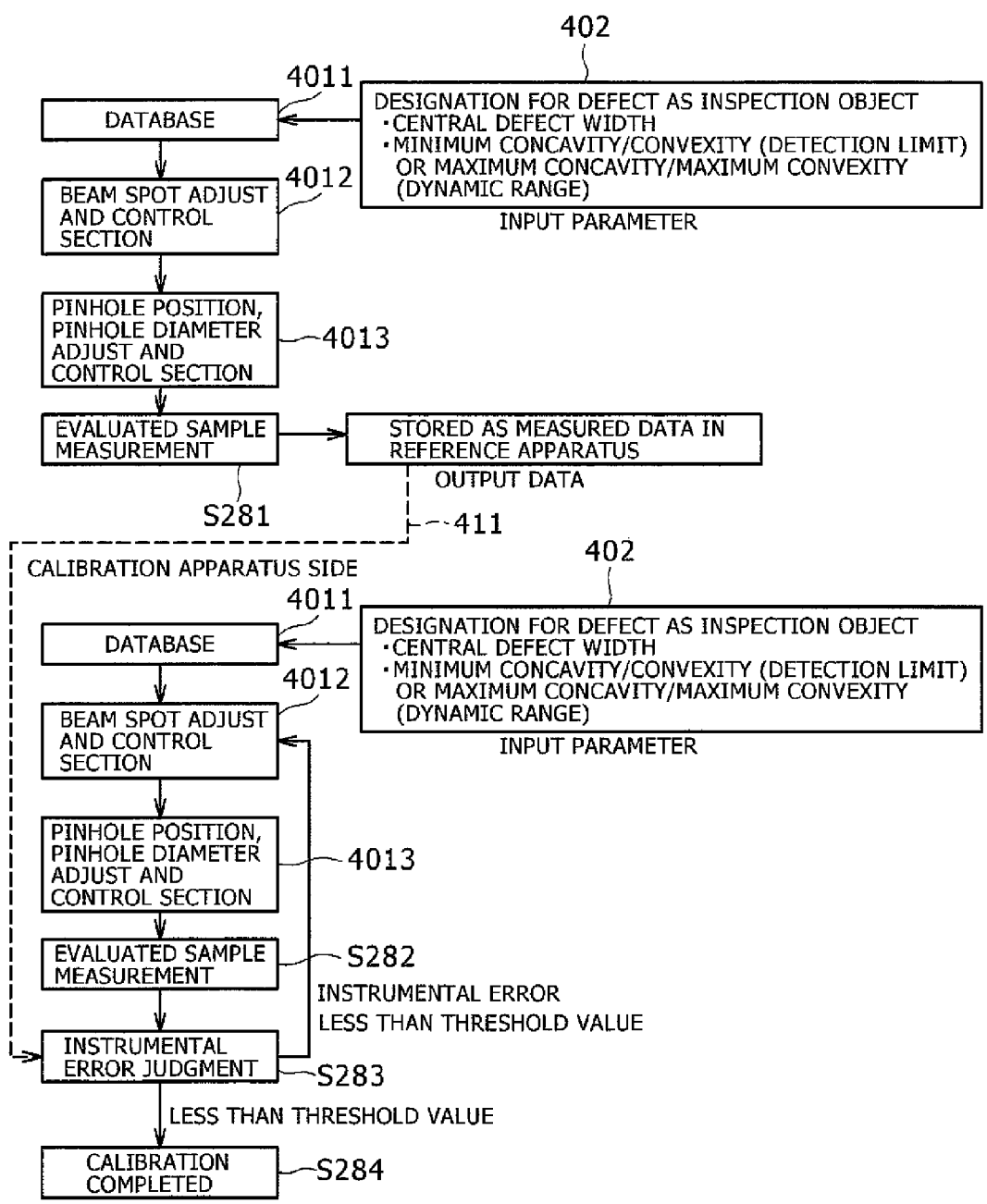
FIG. 28 is a flow chart showing a processing procedure on the side of a reference apparatus and a processing procedure on the side of a calibration apparatus in a processing procedure for reducing an instrumental error between apparatuses.

The third embodiment for reducing an instrumental error or difference in sensitivity between the apparatuses (between disk surface inspection apparatuses) according to the invention is to be described by referring FIG. 28. At first, in the reference apparatus or standard apparatus, an inspection target defect data 402 is inputted, and the beam spot diameter, the pinhole position, and the pinhole diameter are adjusted by the adjusting and controlling sections 4012, 4013 based on the data base 4011 which is used in common between the plural apparatuses by way of the network 411. A certain evaluation sample is measured under the optical conditions and the result is stored as a measurement data in the reference apparatus into the data base 4011 which is used in common between the apparatuses (this may be a server used in common by way of the network 411) (S281).

Then, in a calibration apparatus, values 402 identical with those of the defect as the inspection target set by the reference apparatus are inputted, and the beam spot diameter, the pinhole position, and the pinhole diameter are adjusted by the adjusting and controlling sections 4012 and 4013 based on the data base 4011 which is used in common between the apparatuses by way of the network 411. Under the optical conditions, an identical evaluation sample measured in the reference apparatus is measured (S282). Referring to the result of measurement for the measured evaluation sample, it is ideal that the result measured by the reference apparatus and the result measured by the calibration apparatus are identical with each other. However, since there is an instrumental error between the apparatuses, they do not always agree to each other. Then, the instrumental error between the obtained result measured by the reference apparatus obtained by way of the network 411 shown by the dotted line (stored in the data base 4011 which is used in common between apparatuses) and the result measured by the calibration apparatus (stored in the data base 4011 which is used in common between apparatuses) is judged, for example, by the signal intensity judging section 4014 in the calibration apparatus (S283), and the beam spot diameter, the pinhole position, and the pinhole diameter of other device (for example, calibration apparatus) are adjusted finely such that the instrumental error is at or less than a threshold value.

As has been described above, by using the data base 4011 which the beam spot diameter adjusting amount by each of the first and the second projection optical systems 200, 100 and the moving and adjusting amount of the photoreceiving surface and the photoreception adjusting amount to the photoreceiving surface by each of first and the second receiving optical systems 210, 120 capable of obtaining sufficient sensitivity for detecting an optimal shape defect by previous simulation or experiment in common between the apparatuses (between disk surface inspection apparatuses), the beam spot diameter, the pinhole position, and the pinhole diameter can be adjusted finely at a high speed with no instrumental error.

Figure 29:
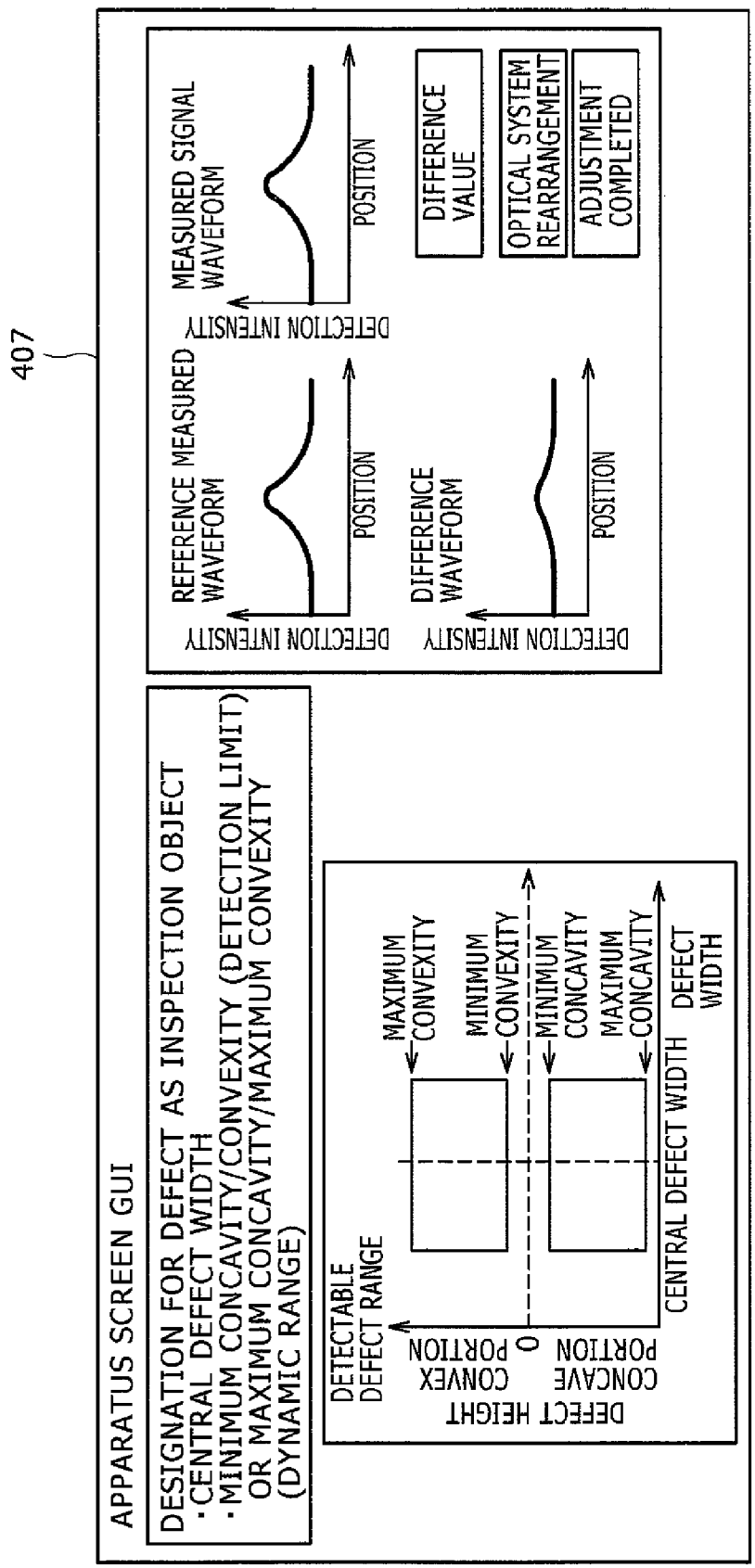
FIG. 29 shows a GUI screen of an apparatus for reducing an instrumental error between apparatuses.

Then, the evaluated sample and the evaluation parameter are to be described. FIG. 29 shows a GUI screen 407 of a calibration apparatus when using a concave defect sample as an evaluation sample. In the calibration apparatus, values identical with those in the reference apparatus for the defect as inspection target are inputted by using the GUI screen 407. Then, a difference (instrumental error) between the data measured for the concave defect in the reference apparatus and the data measured for the concave defect in the calibration apparatus is determined, for example, by the signal intensity judging section 4014 of the reference apparatus and, if the sum for the differences at respective positions is at or less than a threshold value, it is judged as the calibration has been completed (S284). If it is more than the threshold value, the spot diameter, the pinhole position, and the pinhole diameter are adjusted finely again and the procedure is repeated till the sum is reduced to or less than the threshold value.

Figure 30:
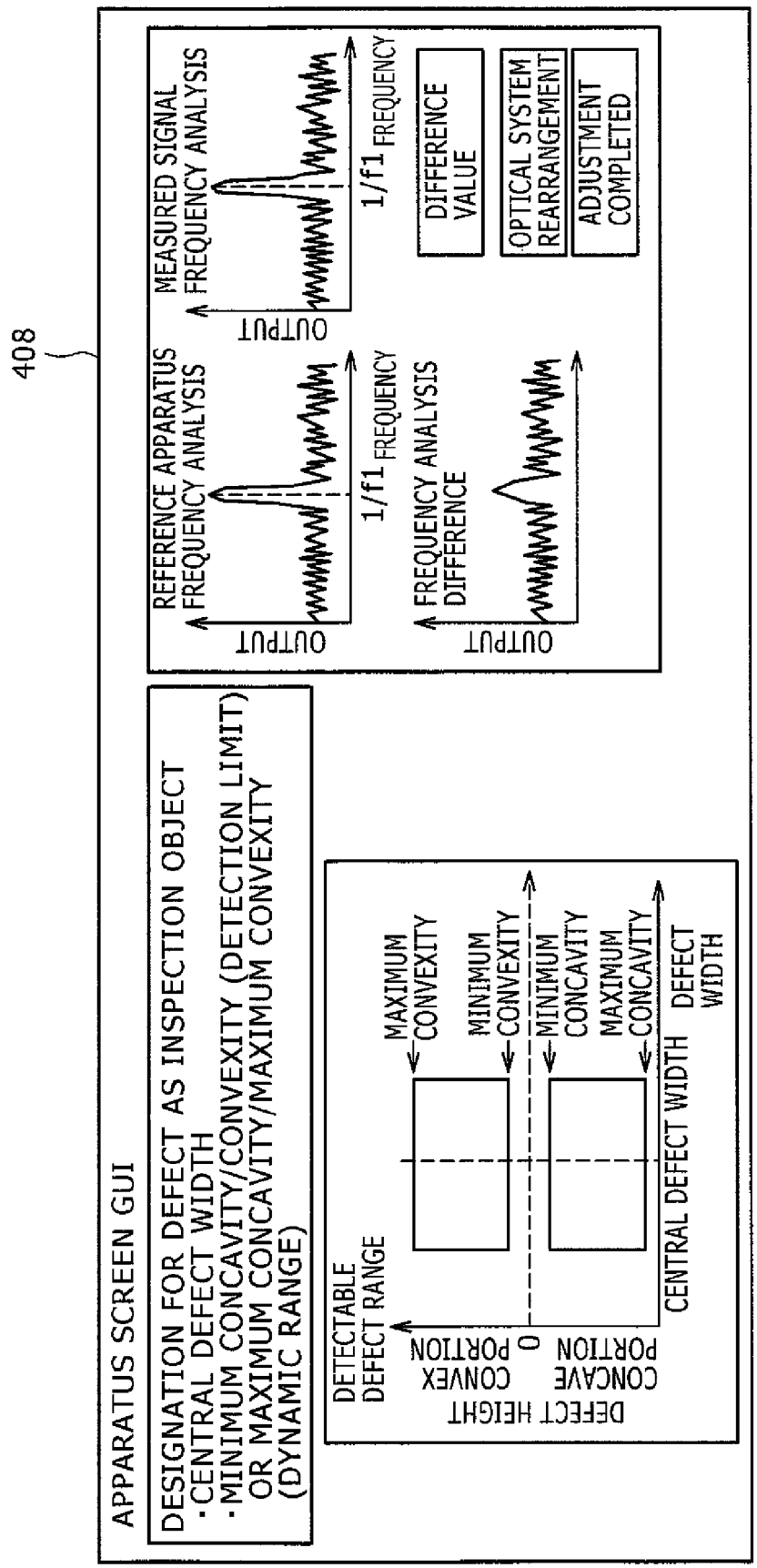
FIG. 30 is a view showing a second example of the GUI screen of the apparatus for reducing the instrumental error between apparatuses.

As the evaluation sample, the roughness sample that has been explained in FIGS. 21A to 21G may also be used. In a case of using such roughness sample, as shown in the GUI screen 408 of the calibration apparatus in FIG. 30, the result of measurement is subjected to frequency analysis, the difference (instrumental error) between the data of the reference apparatus put to frequency analysis and the data of the calibration apparatus put to frequency analysis is determined and the optical system is finely adjusted such that the sum for the differences is at or less than the threshold value.

Figure 31:
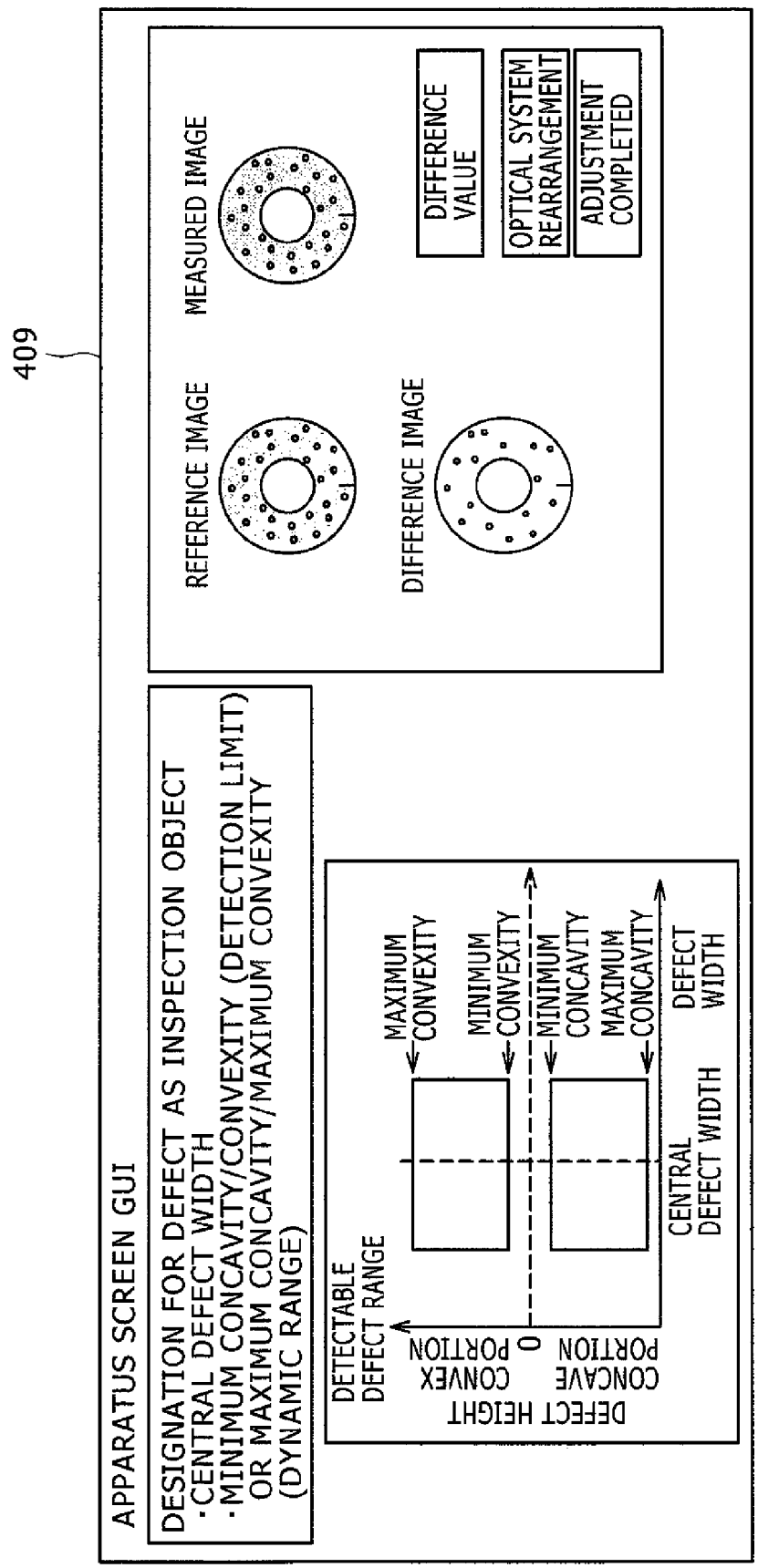
FIG. 31 is a view showing a third example of the GUI screen of the apparatus for reducing the instrumental error between apparatuses.

Further, as the evaluation parameters, an image as a result of measurement for the entire surface of the roughness sample as shown in the GUI screen 409 of the calibration apparatus shown in FIG. 31 may also be used. In this case, data obtained by the reference apparatus is formed into an image. As a method of preparing the image of the data, the sample is, for example, scanned spirally and coordination conversion is conducted to the obtained 1-dimensionally arranged signals (on polar coordination) to generate a disk image (on orthogonal coordination). The image obtained by the reference apparatus and the image obtained by the calibration apparatus are formed by this method to determine the difference image (instrumental error). The difference for each of the pixels in the obtained difference image is determined and the optical system is finely adjusted such that the sum for the differences is at or less than a threshold value.

By the method as has been described above, the instrumental error between the apparatuses can be reduced.

Fourth Embodiment

Figure 32A:
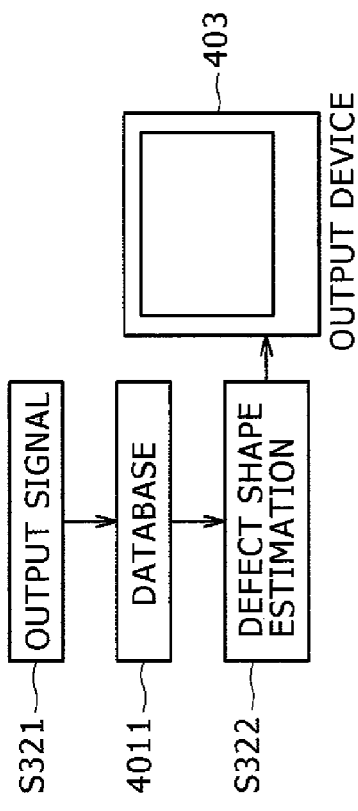
FIG. 32A is a flow chart showing a processing procedure for estimating a defect shape based on a detection signal waveform.
Figure 32C:
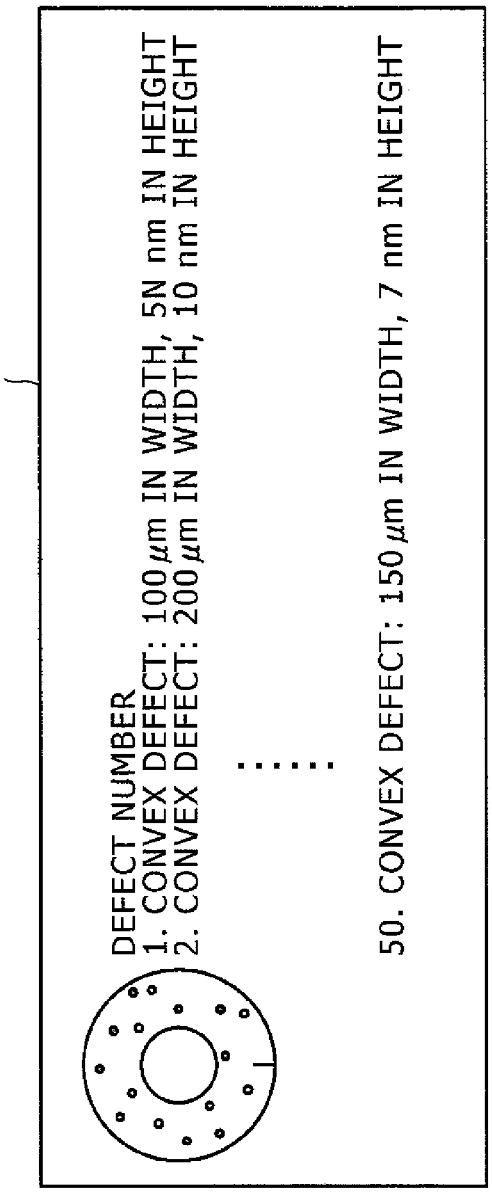
FIG. 32C is a view for a screen that displays the positions of defects obtained by inspection for the entire surface of a disk as the shape information.
Figure 32B:
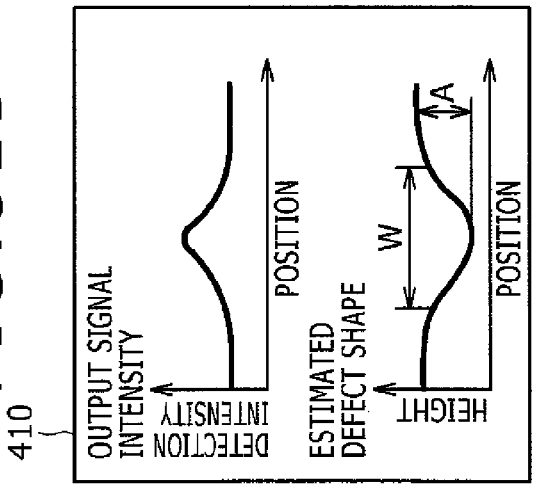
FIG. 32B is a graph showing a relation between the waveform of an output signal intensity and a defect shape estimated therefrom.

The defect shape present on the disk surface can be estimated in view of the detection intensity obtained when the disk surface having a defect of an unknown shape is measured by preparing the data base 4011 for the detection intensity detected by each of the first and the second photoreceiving optical systems 210 and 120 for an optional defect shape at a certain arrangement for the optical system as shown in FIG. 13A to FIG. 16E (relation between the beam spot diameter adjusting amount by each of the first and the second projection optical systems 200 and 100 and the moving adjusting amount of the photoreceiving surface and the photoreception adjusting amount to the photoreceiving surface by each of the first and the second receiving optical systems 210 and 120). The fourth embodiment is shown in FIGS. 32A to 32C. FIG. 32A shows a flow chart. At first, the procedure starts by measurement of a disk having a defect of an unknown shape and inputs measured signals to the apparatus (S321). For example, the defect shape present on the disk surface can be estimated by selecting a signal intensity waveform most similar in view of the shape based on the data base 4011 in view of the output signal waveform in the shape-dependent defect judging section 4017 (S322). As an example for the method of evaluating the degree of agreement between the measured waveform and the data base waveform, evaluation by at least square method may be considered. Thus, it is estimated that a defect shape corresponding to the most matching waveform is present on the disk surface having the defect of an unknown shape. As examples 410, 411 of the output screen, a defect shape estimated in view of the output signal intensity is displayed as shown in FIG. 32B. Alternatively, as shown in FIG. 32C, an embodiment of displaying the number of defect present and the shape information thereof (width and height) upon inspection for the entire disk surface can be practiced.

Fifth Embodiment

Figure 12:
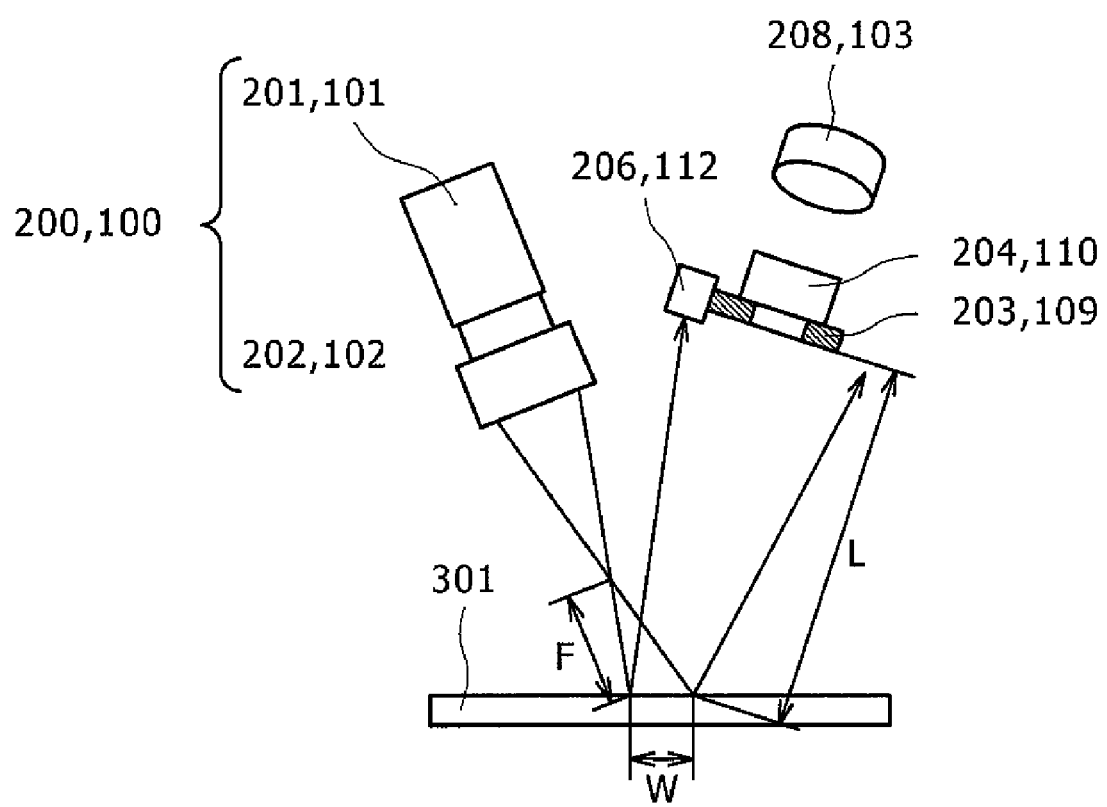
FIG. 12 is a view showing a schematic configuration of an optical system of once condensing an irradiation light at a disk surface.
Figure 13A:
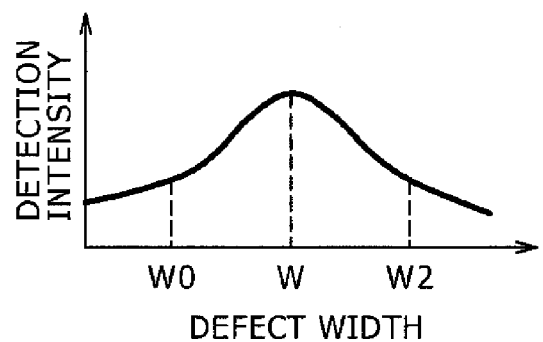
FIG. 13A is a graph showing a relation between a defect width and a detection intensity.
Figures 13B, 13C, 13D:
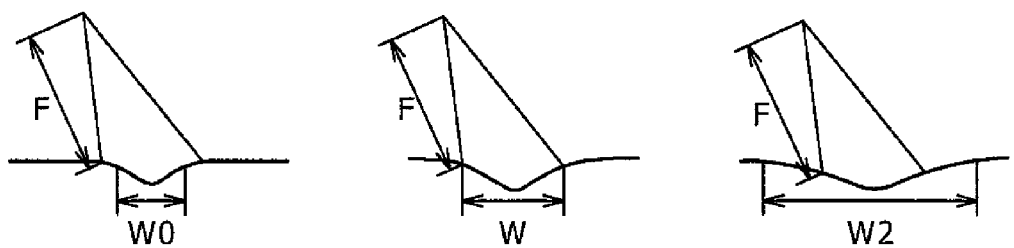
FIG. 13B is a view showing a relation between a defect width W0 and a distance F from the disk surface to the condensation point in the optical system shown in FIG. 12.
FIG. 13C is a view showing a relation between a defect width W and a distance F from the disk surface to the condensation point in the optical system shown in FIG. 12.
FIG. 13D is a view showing a relation between a defect width W2 and a distance F from the disk surface to the condensation point in the optical system shown in FIG. 12.
Figure 33A:
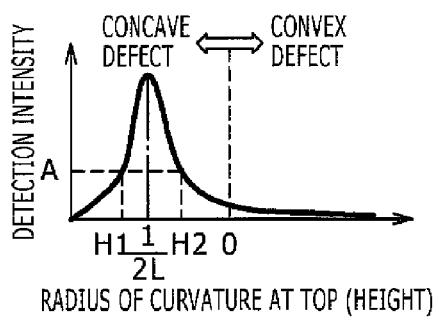
FIG. 33A is a view showing the detection result of a sample detected by using an optical system set to first optical conditions shown in FIG. 33C, and shows a case where two radii of curvature at the top (height) to a detection intensity are present.
Figure 33B:
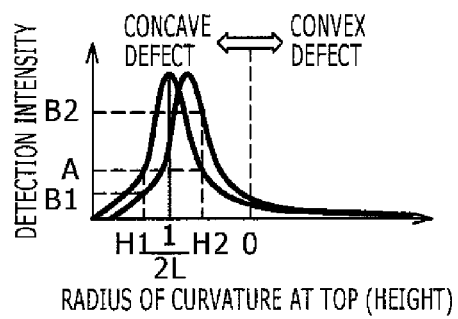
FIG. 33B is a graph indicating the result of detection in a case of inspecting the sample shown in FIG. 33A by an optical system set to second optical conditions shown in FIG. 33D in juxtaposition with the result of FIG. 33A.
Figure 33C:
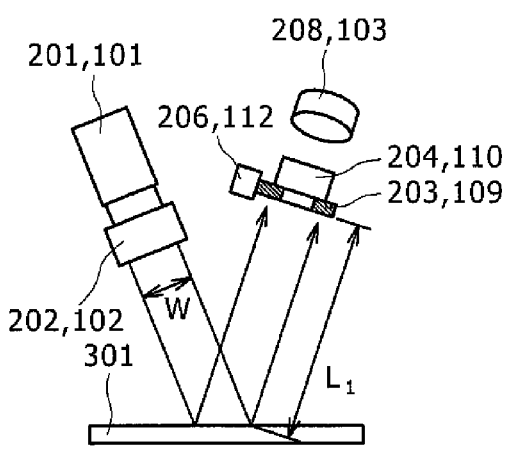
FIG. 33C is a view showing the configuration of the optical system set to the first optical condition.
Figure 33D:
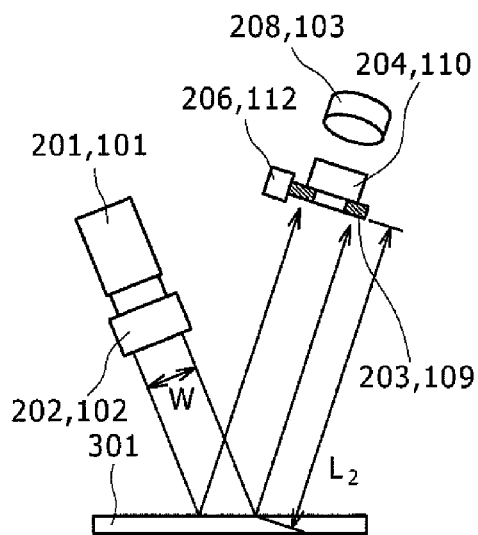
FIG. 33D is a view showing the configuration of the optical system set to the second optical condition.

With respect to the detection characteristic of the optical system shown in FIG. 7 and FIG. 12, there may be considered a possibility that two defect heights corresponding to a detection intensity are present. In this case, the defect height cannot be determined uniquely. In this case, the defect height can be determined uniquely by conducting inspection twice while changing the optical conditions. For example, it is assumed that the result of inspection by using an optical system set to first optical conditions as shown in FIG. 33C results in a state as shown in FIG. 33A. In this case, when inspection is conducted by using the optical system set to second optical conditions as shown in FIG. 33D, since the detection intensity to the two defects are different as shown by the result of displaying the data of FIG. 33B being in juxtaposition with the data of FIG. 33A, discrimination is possible by twice inspection of FIG. 33C and FIG. 33D.

As has been described above, according to the invention, an optical system can be automatically adjusted so as to have sufficient sensitivity for detection to a defect of optional shape by the provision of an automatic adjusting mechanism for the arrangement of the optical system.

Further, the invention provides an excellent effect of allowing easy adjustment by the apparatus GUI by forming a relation between the defect shape and the arrangement for the optical system having the sufficient sensitivity for detection to the defect into a data base.

Further, it is possible according to the invention to reduce the instrumental error between the apparatus by using the data base in common among plural apparatus.

Further, according to the invention, it is possible to estimate the defect shape in view of the detection signal waveform based on the data base.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. A disk surface inspection apparatus, comprising:
    a projection optical system for irradiating a laser beam to a disk surface;
    a receiving optical system for receiving a normal reflection light of the laser beam reflected from the disk surface irradiated by the projection optical system through a photoreceiving surface; and
    a signal processing section for processing signal output from the receiving optical system to inspect the state of the disk surface,
the apparatus further including:
    a first adjusting means for adjusting a beam spot diameter of the laser beam on the disk surface irradiated by the projection optical system; and a second adjusting means for moving the photoreceiving surface of the receiving optical system in a direction along with an optical axis of the receiving optical system, thereby adjusting a photoreception amount on the photoreceiving surface.

2. The disk surface inspection apparatus according to claim 1, wherein the signal processing section inspects the state of the disk surface including a defect contained in the disk surface.

3. The disk surface inspection apparatus according to claim 2, the apparatus further comprising a data base that determines and stores a beam spot diameter adjusting amount, and a moving and adjusting amount of the photoreceiving surface and a photoreception adjusting amount to the photoreceiving surface capable of obtaining sufficient sensitivity for detection of a defect of an optional shape by previous simulation or experiment,
wherein the apparatus obtains the beam spot diameter adjusting amount, and the moving and adjusting amount of the photoreceiving surface and the photoreception adjusting amount to the photoreceiving surface capable of obtaining sufficient sensitivity in accordance with a defect shape as an inspection target inputted from the data base, and
the first adjusting means conducts adjustment based on the obtained beam spot diameter adjusting amount, and the second adjust means conducts adjustment based on the obtained moving and adjusting amount of the photoreceiving surface and the photoreception adjusting amount to the photoreceiving surface.

4. The disk surface inspection apparatus according to claim 3,
wherein the data base stores known relevant data for a detection intensity detected by the receiving optical system to the defect of the optional shape in a relation between the beam spot diameter adjusting amount, and the moving and adjusting amount of the photoreceiving surface and the photoreception adjusting amount to the photoreceiving surface, and
the signal processing section estimates the defect shape based on the known relevant data stored in the data base in view of the detection intensity based on signals obtained from the receiving optical system.

5. A disk surface inspection apparatus, including:
a first and a second projection optical systems for irradiating each of first and second laser beams to a disk surface;
a first and a second light receiving optical systems for receiving each of first and second normal reflection lights of the first and the second laser beams reflected from the disk surface irradiated by each of the first and the second projection optical systems; and
a signal processing section for processing signal output from the first and the second receiving optical systems to inspect the state of the disk surface,
the apparatus further including:
a first adjusting means for adjusting each of the beam spot diameters of the laser beams on the disk surface irradiated by each of the first and the second projection optical systems, and
second adjusting means for moving each of the photoreceiving surfaces along with each of optical axes of the first and the second receiving optical systems thereby adjusting a photoreceiving amount to each of the photoreceiving surfaces.

6. The disk surface inspection apparatus according to claim 5,
wherein a defect is contained in the state of the disk surface inspected in the signal processing section.

7. The disk surface inspection apparatus according to claim 6, further comprising a data base that determines and stores a beam spot diameter adjusting amount by each of the first and the second projection optical systems, and a moving and adjusting amount of the photoreceiving surface and a photoreception adjusting amount to the photoreceiving surface by each of the first and the second receiving optical systems capable of obtaining sufficient sensitivity for detection of a defect of an optional shape by previous simulation or experiment,
wherein the apparatus obtains the beam spot diameter adjusting amount by each of the first and the second projection optical systems, and the moving and adjusting amount of the photoreceiving surface and the photoreception adjusting amount to the photoreceiving surface by each of the first and the second receiving optical systems capable of obtaining the sufficient sensitivity in accordance with a defect shape as an inspection target inputted from the data base, and
the first adjusting means conducts adjustment based on the obtained beam spot diameter adjusting amount by each of the first and the second projection optical systems, and the second adjusting means conducts adjustment based on the obtained moving and adjusting amount of the photoreceiving surface and the photoreception adjusting amount to the photoreceiving surface by each of the first and the second receiving optical system.

8. The disk surface inspection apparatus according to claim 7,
wherein the data base stores known relevant data of a detection intensity detected by each of the first and the second receiving optical systems to a defect of an optional shape in a relation between the beam spot diameter adjusting amount by each of the first and the second projection optical systems and the moving and adjusting amount of the photoreceiving surface and the photoreception adjusting amount to the photoreceiving surface by each of the first and the second receiving optical systems, and
the signal processing section estimates the defect shape based on the known relevant data stored in the data base in view of the detection intensity based on the signals obtained from each of the first and the second receiving optical systems.

9. The disk surface inspection apparatus according to claim 5, wherein the first laser beam is irradiated to the disk surface while restricted more finely than the second laser beam.

10. The disk surface inspection apparatus according to claim 5, wherein the first receiving optical surface has a branching optical system for branching the reflection light of the first laser beam obtained from the disk surface into first and second optical paths, a first photoreceiving device for receiving a scattered light while cutting off the normal reflection light in the first optical path branched at the branching optical system, and a second photoreceiving device for receiving the normal reflection light through the photoreceiving surface in the second optical path branched at the branching optical system.

11. A disk surface inspection system, comprising:
a plurality of disk surface inspection apparatuses each including a projection optical system for irradiating a laser beam to a disk surface;

a receiving optical system for receiving a normal reflection light of the laser beam obtained from the disk surface irradiated by the projection optical system through a photoreceiving surface;

a signal processing section that inspects the state of the disk surface based on signals obtained from the receiving optical system, the apparatuses including:

a first adjusting means for adjusting a beam spot diameter on the disk surface of the laser beam irradiated by the projection optical system; and a second adjusting means for moving and adjusting a position of the photoreceiving surface for receiving the normal reflection light by the receiving optical system in a direction of an optical axis, thereby adjusting a photoreception amount to the photoreceiving surface, wherein a data base that determines and stores a beam spot diameter adjusting amount and a moving and adjusting amount of the photoreceiving surface and a photoreception adjusting amount to the photoreceiving surface capable of obtaining sufficient sensitivity for detection to a defect of an optional shape by previous simulation or experiment is used in common among the plurality of disk surface inspection apparatuses.

12. A disk surface inspection method comprising a projection step of irradiating a laser beam to a disk surface, a photoreceiving step of receiving a normal reflection light of the laser beam obtained from the disk surface irradiated by the projection step through a photoreceiving surface, and a signal processing step for inspecting the state of the disk surface based on signals obtained by photoreceiving in the photoreceiving step, the method further including:

a first adjusting step of adjusting a beam spot diameter of the irradiated laser beam on the disk surface in the projection step, and a second adjusting step of moving and adjusting a position of the photoreceiving surface for receiving the normal reflection light in the photoreceiving step, thereby adjusting the photoreceiving amount to the photoreceiving surface.

13. The surface inspection method according to claim 12, wherein a defect is contained in the state of the disk surface to be inspected in the signal processing step.

14. The method of inspecting a disk surface according to claim 13, further comprising:

using a data base that determines and stores a beam spot diameter adjusting amount, and a moving adjusting amount of the photoreceiving surface and a photoreception adjusting amount to the photoreceiving surface capable of obtaining sufficient sensitivity for detection to a defect of an optional shape by previous simulation or experiment, obtaining the beam spot diameter adjusting amount, and the moving and adjusting amount of the photoreceiving surface and the photoreception adjusting amount to the photoreceiving surface capable of obtaining sufficient sensitivity in accordance with a defect shape as an inspection target inputted from the data beams, conducting adjustment based on the obtained spot diameter adjusting amount in the first adjusting step, and conducting adjustment based on the obtained moving and adjusting amount of the photoreceiving surface and the photoreception adjusting amount to the photoreceiving surface in the second adjusting step.

15. The disk surface inspection method according to claim 14, further comprising the step of storing known relevant data of a detection intensity detected by the receiving optical system to the defect of an optional shape in a relation between the beam spot diameter adjusting amount, and the moving and adjusting amount of the photoreceiving surface and the photoreception adjusting amount to the photoreceiving surface in the data base, wherein the defect shape is estimated based on the known relevant data stored in the data base in view of the detection intensity based on the signals obtained in the photoreceiving step in the signal processing step.

* * * * *